(12) United States Patent
Kringelum et al.

(10) Patent No.: US 6,660,515 B2
(45) Date of Patent: Dec. 9, 2003

(54) METHOD OF IMPROVING THE EFFICACY OF LACTIC ACID BACTERIAL STARTER CULTURES AND IMPROVED STARTER CULTURE COMPOSITIONS

(75) Inventors: Boerge Kringelum, Ballerup (DK); Dan Nillson, Espergaerde (DK); Kim Ib Soerensen, Farum (DK)

(73) Assignee: CHR. Hansen A/S, Hoersholm (DK)

( * ) Notice: Subject to any disclaimer, the term of this patent is extended or adjusted under 35 U.S.C. 154(b) by 49 days.

(21) Appl. No.: 09/879,036

(22) Filed: Jun. 13, 2001

(65) Prior Publication Data

US 2002/0081712 A1 Jun. 27, 2002

Related U.S. Application Data

(63) Continuation of application No. 09/086,722, filed on May 29, 1998, which is a continuation of application No. PCT/DK98/00210, filed on May 25, 1998, now abandoned.
(60) Provisional application No. 60/048,337, filed on May 30, 1997.

(30) Foreign Application Priority Data

May 30, 1997 (DK) .............................................. 0633/97

(51) Int. Cl.$^7$ ................................................. C12N 1/20
(52) U.S. Cl. .................... 435/252.4; 426/34; 435/41; 435/139; 435/170; 435/243; 435/252.9
(58) Field of Search .................... 435/243, 41, 170, 435/252.4, 139, 252.9; 426/34

(56) References Cited

FOREIGN PATENT DOCUMENTS

| EP | 0 111 392 | 11/1983 |
| EP | 0 112 020 | 11/1983 |
| EP | 0 141 642 | 10/1984 |
| WO | 98/07843 | 2/1998 |

OTHER PUBLICATIONS

McKay, et al., *Altered Metabolism in a Streptococcus lactis C2 Mutant Deficient in Lactic Dehydrogenase*, Journal of Dairy Science, vol. 57, No. 2, pp. 181–186, (1973).
Dickely, F. et al., "Isolation of *Lactococcus lastis* nonsense suppressors and construction of a food–grade cloning vector", *Mol. Microbiol.*, vol. 15(5); pp. 839–847 (1995).
Rajagopal, S.N. et al., "Associative Growth and Proteolysis of *Streptococcus thermophilus* and *Lactobacillus bulgaricus* in Skim Milk", *J. Dairy Sci.*, vol. 73; pp. 894–899 (1990).
Terzaghi, B.E. et al., "Improved Medium for Lactic Streptococci and Their Bacteriophages", *Applied Microbiol.*, vol. 29(6); pp. 807–813 (1975).
Kurosawa, H. et al., "L–Lactic Acid Production from Starch by Coimmobilized Mixed Culture System of *Aspergillus awamori* and *Streptococcus lastis*", *Biotech. and Bioengineering*, vol. 31; pp. 183–187 (1988).
Condon, S., "Responses of lactic acid bacteria to oxygen", *EMS Microbiol. Rev.*, vol. 46; pp. 269–280 (1987).
Suzuki, I. et al., "Growth of *Lactobacillus bulgaricus* in Milk, 1. Cell Elongation and the Role of Formic Acid in Boiled Milk", *J. Dairy Sci.*, vol. 69; pp. 311–320 (1985).
Galesloot, Th. E. et al., "Symbiosis in Yoghurt (I), Stimulaton of *Lactobacillus Bulgaricus* by a Factor Produced by *Streptococcus Thermophilus*", *Neth. Milk & Dairy J.*, vol. 22; pp. 50–63 (1968).
Veringa, H.A. et al., "Symbiosis in Yoghurt (II), Isolation and Identification of a Growth Factor for *lactobacillus Bulgaricus* Produced by *Streptococcus Thermophilus*", *Neth. Milk & Dairy*, vol. 22; pp. 114–120 (1968).
Teraguchi, et al., *Oxygen Uptake Activity and Aerobic Metabolism of Streptococcus thermophilus* STH450, J. Dairy Sci, vol. 70, pp. 514–523, 1987.
T. Ferain et al., "*Lactobacillus Plantarum* ldhL Gene: Overexpression and Deletion," J. Bacteriology, vol. 176, No. 3, (1994), pp. 596–601.
N. Goupil et al., "Imbalance of Leucine Flux in *Lactococcus lactis* and its Use for the Isolation of Diacetyl–Overproducing Strains," Applied and Environmental Microbiology, vol. 62, No. 7, Jul. 1996, pp. 2636–2640.

*Primary Examiner*—Leon B. Lankford, Jr.
(74) *Attorney, Agent, or Firm*—Iver P. Cooper

(57) ABSTRACT

Methods of enhancing the growth rate and/or controlling the metabolic activity of lactic acid bacteria and of improving the shelf life and/or the quality of an edible product using lactic acid bacterial organisms which are defective in their pyruvate metabolism. There is also provided starter culture compositions comprising such defective lactic acid bacteria as helper organisms and lactic acid bacterial starter culture strains. Useful helper organisms are Lactococcus strains which are defective with respect to pyruvate formate lyase (Pfl) and/or lactate dehydrogenase (Ldh) activity. The helper organisms may overexpress a gene coding for an NAD$^+$ regenerating enzyme such as NADH oxidase encoded by nox gene.

19 Claims, 8 Drawing Sheets

Figure 1:
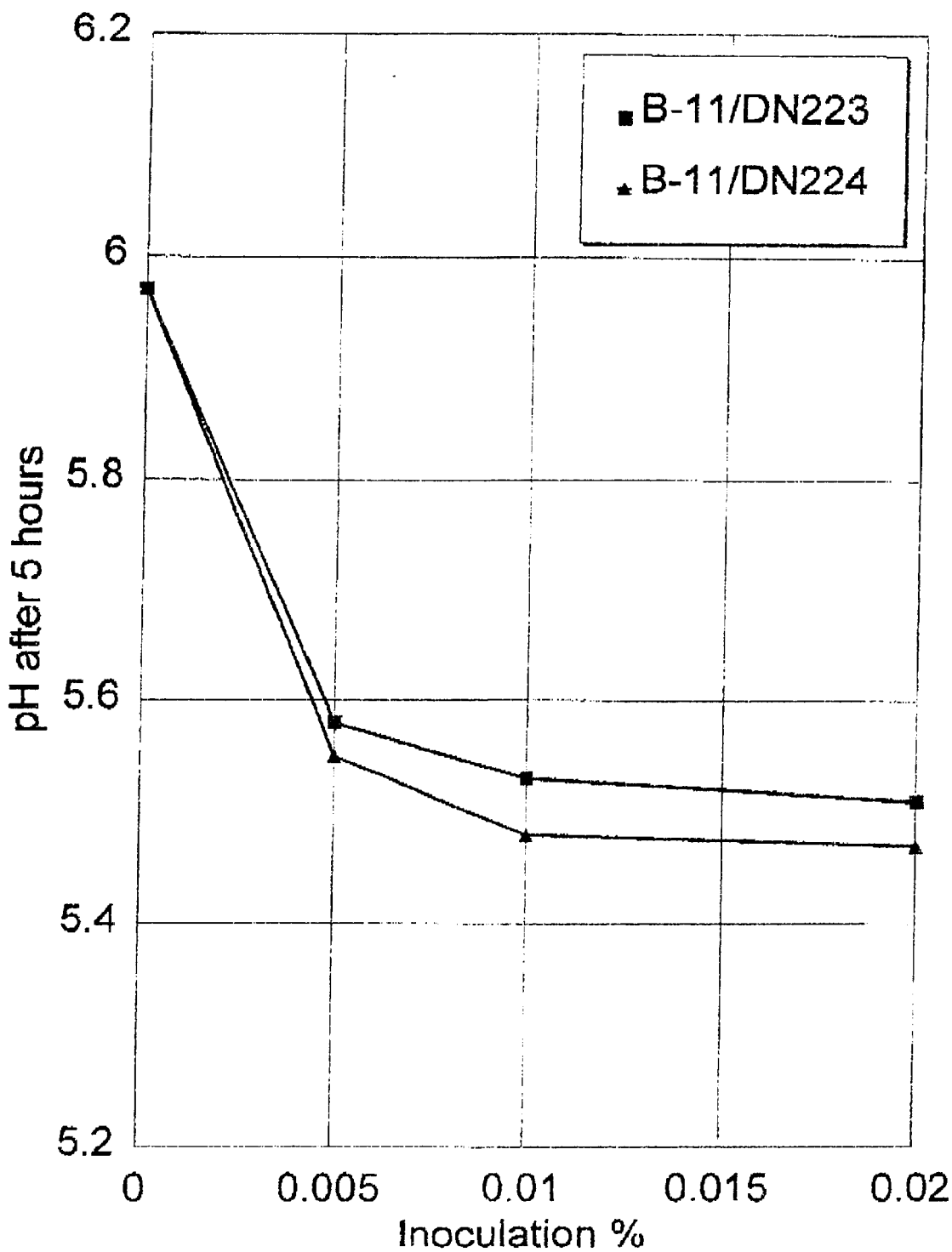

METHOD OF IMPROVING THE EFFICACY OF LACTIC ACID BACTERIAL STARTER CULTURES AND IMPROVED STARTER CULTURE COMPOSITIONS

This is a continuation of Ser. No. 09/086,722 filed May 29, 1998, now pending, which is (1) a continuation of PCT/DK98/00210 filed May 25, 1998, now abandoned, and (2) a nonprovisional of No. 60/048,337 filed May 30, 1997, now abandoned.

The prior application(s) set forth above are hereby incorporated by reference in their entirety.

FIELD OF INVENTION

The present invention relates to the field of lactic acid bacterial starter cultures and in particular there is provided the means of enhancing the growth rate and/or controlling the metabolic activity of lactic acid bacteria by cultivating the lactic acid bacteria in association with a lactic acid bacterial helper organism which has a defeat in its pyruvate metabolism. Such a helper organism is also useful as a means of improving the shelf life and/or quality of edible products.

TECHNICAL BACKGROUND AND PRIOR ART

Lactic acid bacteria are used extensively as starter cultures in the food industry in the manufacture of fermented products including milk products such as e.g. yoghurt and cheese, meat products, bakery products, wine and vegetable products.

As used herein the term "lactic acid bacteria" refers to gram-positive, microaerophilic or anaerobic bacteria which ferment sugars with the production of acids including lactic acid as the predominantly produced acid, acetic acid, formic acid and propionic acid. The industrially most useful lactic acid bacteria are found among Lactococcus species, such as *Lactococcus lactis*, Lactobacillus species, Streptococcus species, Leuconostoc species, Pediococcus species and Propionibacterium species. Also the strict anaerobes belonging to the genus Bifidobacterium is generally included in the group of lactic acid bacteria.

When a lactic acid bacterial starter culture is added to milk or any other edible starting material and appropriate conditions for growth and metabolic activity of the starter culture are provided, the bacteria will start to propagate after a period of time known as the lag phase, during which the bacteria adapt to the new conditions. Once propagation of the bacteria is initiated it is rapid with concomitant conversion of citrate, lactose or other sugars into lactic acid/lactate as the major acidic metabolite, and possibly other acids including acetate, resulting in a pH decrease. In addition, several other metabolites such as e.g. acetaldelyde, α-acetolactate, acetoin, diacetyl and 2,3-butylene glycol (butanediol) are produced during the growth of the lactic acid bacteria.

Generally, the growth rate and the metabolic activity of lactic acid bacterial starter cultures can be controlled by selecting appropriate growth conditions for the strains of the specific starter culture used such as appropriate growth temperature, oxygen tension and content of nutrients. Thus, it is known in the dairy industry that a reduction of the oxygen content of the milk raw material will result in a more rapid growth of the added lactic acid bacteria which in turn results in a more rapid acidification of the inoculated milk. Currently, such a reduction of the oxygen content is carried out by heating the milk in open systems, by deaerating the milk in vacuum or by a sparging treatment. Alternative means of reducing the oxygen content include the addition of oxygen scavenging compounds.

Lactic acid bacterial starter cultures are commonly used in the food industry as mixed strain cultures comprising one or several species. For a number of mixed strain cultures such as yoghurt starter cultures typically comprising strains of *Lactobacillus bulgaricus* and *Streptococcus thermophilus*, a symbiotic relationship between the species has been reported, assumingly due to proteolytic activity of at least one of the strains (Rajagopal et al. J. Dairy Sci., 1990 73:894–899). It has also been reported that in such mixed yoghurt cultures, stimulation of growth of the Lactobacillus component is due to the inherent formation of formic acid by the *Streptococcus thermophilus* (Suzuki et al., 1986). A further example of a symbiotic relationship between strains in a mixed culture is disclosed in EP 0 111 392 A2 where it is demonstrated that selected wild-type *Streptococcus thermophilus* strains having a relatively high oxygen uptake ability improves the survival of a strictly anaerobic Bifidobacterium species when it is combined with the Streptococcus strain.

However, the prior art is not aware of any generally applicable biological method whereby the growth and metabolic activity of lactic acid bacterial starter cultures can be enhanced. It is therefore a primary objective of the present invention to provide such a method.

SUMMARY OF THE INVENTION

Accordingly, the present invention relates in a first aspect to a method of enhancing the growth rate and/or controlling the metabolic activity of a lactic acid bacterial strain, comprising cultivating the strain in association with a lactic acid bacterial helper organism that is defective in its pyruvate metabolism.

In a further aspect there is provided a method of improving the shelf life and/or the quality of an edible product comprising adding to the product a lactic acid bacterial strain that is defective in its pyruvate metabolism and in a still further aspect the invention pertains to a starter culture composition comprising a lactic acid bacterium and a lactic acid bacterial helper organism that in defective in its pyruvate metabolism, said helper organism being capable of enhancing the growth rate and/or controlling the metabolic activity of the lactic acid bacterium.

In yet another aspect the invention pertains to a lactic acid bacterium that is defective in at least one enzyme involved in the pyruvate metabolism and in which a gene capable of regenerating $NAD^+$ is overexpressed.

DETAILED DISCLOSURE OF THE INVENTION

It is a primary objective of the present invention to provide a generally applicable method of enhancing the growth rate and/or controlling the metabolic activity of a lactic acid bacterial starter culture. The method comprises cultivating the culture in association with a lactic acid bacterial helper organism which is defective in its pyruvate metabolism.

It will be understood that enhancement of the growth rate relates to any effect resulting in a higher number of starter culture cells in the medium after a given period of time, i.e. the lactic acid bacterial cells propagate at a higher rate than that obtained without the helper organism, or the cells start propagating at an earlier point in time at a rate equal to or higher as compared to propagation of the lactic acid bacteria without the helper organism.

As used herein, the expression "controlling the metabolic activity" refers to the increased or decreased production of any metabolite produced by the starter culture, including the production of acids, such as lactic acid, acetic acid, formic acid and/or propionic acid. Examples of other metabolites of relevance, the production of which may be controlled, include aroma compounds such as acetaldehyde, α-acetolactate, acetoin, diacetyl and 2,3-butylene glycol (butanediol).

In accordance with the invention, the lactic acid bacterial helper organism is defective in its pyruvate metabolism. As used herein the expression "defective in its pyruvate metabolism" indicates that the helper organism in comparison with the parent strain has an altered metabolism of pyruvate, i.e. an increased or decreased production of one or more metabolites derived from pyruvate.

Such an altered metabolism of pyruvate can be the result of the helper organism being defective in its ability to egress at least one enzyme selected from the group consisting of pyruvate formate lyase, pyruvate dehydrogenase, lactate dehydrogenase, acetolactate synthetase, second acetolactate synthetase, acetolactate decarboxylase and diacetyl reductase. As used herein the expression "defective in its ability to express any of the above enzymes", indicates that the helper organism as compared to the parent strain from which it is derived has a reduced production of the enzyme or that the enzyme is not expressed at all, irrespective of the growth conditions.

Examples of lactic acid bacterial helper organisms which are defective in their ability to express at least one of the above mentioned enzymes include the *Lactococcus lactis* subspecies *lactis* strain DN223 which is defective both in the pyruvate formate lyase (Pfl$^-$) enzyme and in the lactate dehydrogenase enzyme (Ldh$^-$) and the *Lactococcus lactis* subspecies *lactis* strain DN224 which is Ldh defective.

In one useful embodiment of the above method, the cultivation of a lactic acid bacterial strain of the starter culture in association with the helper organism results in an enhancement of the acid production of the strain.

Evidently, the above-mentioned enhanced production of acids will result in a pH decrease of the medium inoculated with the associative culture (a starter culture in association with the helper organism according to the invention) which exceeds that obtained in the same medium inoculated with the starter culture alone. The difference in pH of the medium inoculated with the starter culture alone and the medium inoculated with the associative culture is referred to herein as ΔpH. In useful embodiments of the invention the enhanced acid production results in a ΔpH of at least 0.05 after 3 hours or more of cultivation, such as a ΔpH of at least 0.1 after 3 hours or more of cultivation, e.g. a ΔpH of at least 0.5 after 3 hours or more of cultivation, such as a ΔpH of at least 0.8 after 3 hours or more of cultivation, e.g. a ΔpH of at least 1.0 after 3 hours or more of cultivation.

In useful embodiments of the present invention the lactic acid bacterial starter culture is a mixed strain culture comprising at least two strains of lactic acid bacteria. Examples of such mixed strain cultures are described in the below examples. Thus, in particularly preferred embodiments of the invention the helper organism is capable of enhancing the growth rate of at least one of the mixed strain culture strains and/or capable of controlling the metabolic activity of at least one of the strains of the lactic acid bacterial mixed strain culture. Growth conditions which are in all respects optimal for all strains of such lactic acid bacterial mixed strain cultures may not be found. Therefore, the metabolic activity of a mixed strain culture may be controlled selectively by choosing a temperature which favor an increased production of desired metabolites by one or more strains, but which on the other hand may result in a decreased production of other metabolites by other strains. However, the overall result of cultivating a lactic acid bacterial mixed strain culture with a helper organism according to the invention as compared to the lactic acid bacterial mixed strain culture being cultivated alone is an increased number of cells, an increased production of one or more metabolites, including acids and aroma compounds and/or a decreased production of one or more metabolites.

Industrial production of edible products typically includes process steps such as mixing, pumping or cooling whereby the degree of oxygen saturation of the edible product is increased and, as a result, the edible product starting material may have a relatively high initial oxygen content (high degree of oxygen saturation) which is unfavorable for lactic acid bacterial starter cultures. It has now surprisingly been found that when the starter culture is cultivated in an edible product starting material having an initial degree of oxygen saturation of 10%, or higher such as 20% or higher in association with a helper organism according to the invention, its growth rate is substantially enhanced and/or its metabolic activity is controlled as compared to cultivating it without the helper organism under the same conditions.

In useful embodiments of the invention the helper organism is a lactic acid bacterium capable of reducing the amount of oxygen present in the medium. Thus, in particularly preferred embodiments of the invention the helper organism is capable of reducing the amount of oxygen present in the medium by at least 1% per hour including by at least 10% per hour, such as by at least 20% per hour, e.g. by at least 30% per hour. The reduction may even be by at least 40% per hour including by at least 50% per hour, such as by at least 60% per hour, e.g. by at least 70% per hour, such as by at least 80% or by at least 90% per hour.

The method of enhancing the growth rate and/or controlling the metabolic activity according to the invention implies that an increased growth rate and/or control of metabolic activity of lactic acid bacterial starter culture can be obtained even in a medium having a low degree of oxygen saturation, such as in the range of 1–10%. However, the method may be particularly useful when the lactic acid bacterial starter culture is cultivated in an edible product starting material having an initial oxygen saturation of 10% or more, e.g. 20% or more, such as 40% or more, e.g. 50% or more, such as 60% or more, e.g. 70% or more, such as 80% or more, and e.g 90% or more, such as an initial oxygen saturation of 95% or more.

In general, the helper organism is a derivative of a lactic acid bacterium. As used herein the expression "derivative of a lactic acid bacterium" encompasses a lactic acid bacterial mutant which is derived by selecting a spontaneously occurring mutant of a wild-type strain of a lactic acid bacterium or alternatively, by constructing a mutant of a wild-type lactic acid bacterial strain or a previously mutated strain. This construction can be made by subjecting a strain to any conventional mutagenization treatment including treatment with chemical mutagens and UV light.

A mutant can also be constructed by genetic modifications in the parent strain including deletions, insertions, substitutions of nucleotides. These genetic modifications can be obtained by techniques known in the art to introduce such modificaticons, including DNA recombination techniques including site directed mutagenesis, polymerase chain reaction techniques, random or quasi-random mutagenesis using any mutagen, in vitro mutagenesis or any other method known to introduce genetic modifications into substances comprising or being derived from naturally occurring nucleic acids or amino acids. In accordance with the invention, the derivative of a lactic acid bacterium can e.g. be derived from a Lactococcus species, such as *Lactococcus lactis*, a Lactobacillus species, a Streptococcus species, a Leuconostoc species, a Pediococcus species, a Propionibacterium species or a Bifidobacterium species.

In this context, one preferred species is *Lactocaccus lactis* including *Lactococcus lactis* subspecies *lactis* including biovar *diacetylactis*. Examples of suitable helper organisms are *Lactococcus lactis* subspecies *lactis* strain DN223 which has been deposited under the accession No. DSM 11036 and *Lactococcus lactis* subspecies *lactis* strain DN224 which has been deposited under the accession No. DSM 11037. The DN223 and DN224 strains are described in WO 98/07843. In the following reference examples details are given for the isolation of these strains.

It has been found that derivatives, such as the Move DN223 and DN224 strains, that have, relative to the parents, a reduced production of acid, are particularly suitable in the above method of enhancing growth rate or controlling metabolic activity.

The enhancement of the growth rate and/or controlled metabolic activity obtained by the above method can be provided when cultivating the starter culture in any media supporting the growth of lactic acid bacteria. Thus, the effect can be obtained in a variety of edible product components or ingredients such as milk, meat, flour dough, wine and plant materials, such as vegetables, fruits or fodder crops.

The starter culture and the helper organism is added in amounts which result in a number of viable cells of each component which is at least $10^3$ colony forming units (CPU) per gram of the edible product starting materials, such as at least $10^4$ CFU/g including at least $10^5$ CFU/g, such as at least $10^6$ CFU/g, e.g. at least $10^7$ CFU/g, such as at least $10^8$ CFU/g, e.g at least $10^9$ CPU/g, such as at least $10^{10}$ CFU/g, e.g. at least $10^{11}$ CFU/g of the edible product starting materials.

In preferred embodiments of the present invention the ratio between helper organism cells and lactic acid bacterial culture cells is in the range of 1000:1 to 1:1000 such as 500:1 to 1:500, e.g. 100:1 to 1:100, such as in the range of 50:1 to 1:50, e.g in the range of 20:1 to 1:20, such as in the range of 10:1 to 1:10 or in the range of 5:1 to 1:5 such as in the range of 2:1 to 1:2.

In the metabolism of lactic acid bacteria it is required to regenerate NAD$^+$. Several of the enzymes involved in the pyruvate metabolism including Ldh is capable of this regeneration by converting pyruvate to lactate. Accordingly, in a lactic acid bacterial strain that has a defect in its pyruvate metabolism which implies that the ability of the strain to regenerate NAD$^+$ is reduced, there is a need for alternative ways of providing the required amount of this essential compound. One such alternative way which is naturally available in lactic acid bacteria is regeneration by means of NADH oxidases of which three types have been reported (Condon, 1987). The first two are non-haem flavoproteins, one of which catalyses the reduction of $O_2$ to $H_2O_2$, the other one the reduction of $O_2$ to $H_2O$. One example of the latter type of enzyme, i.e. an $H_2O$ forming NADH oxidase is the enzyme encoded by the nox gene. This enzyme regenerates two equivalents of NAD$^+$ under oxygen consumption.

It is therefore contemplated that the enhancing effect of a helper organism according to the invention can be further improved by overexpressing an $O_2$ reducing (i.e. $O_2$ consuming) enzyme including the enzyme encoded by a nox gene present in the organism.

Accordingly, in a further embodiment of the present method the helper organism is one wherein a gene coding for an enzyme that is capable of regenerating NAD$^+$ including the above NADH oxidases is overexpressed. In the present context, the ten "overexpressed" indicates that the level of expression of the gene in increased relative to that of the parent strain from which the helper organism overexpressing the gene is derived. Thus, a helper organism that is capable of overexpressing the gene coding for the NAD$^+$ regenerating enzyme preferably expresses the gene at a level which is at least 10% higher than the level at which the gene is expressed in the parent such as at least 25% higher, e.g. at least 50% higher. It is particularly preferred that the level of expression is at least 100% higher than that of the parent.

The overexpression of the gene can be provided by methods which are known in the art such as e.g. by introducing in the helper organism multiple copies of the gene on the chromosome and/or on extrachromosomal elements including plasmids, phages or cosmids.

Alternatively, the overexpression is the result of operably linking a gene or genes naturally occurring in the helper organism or a gene/genes that is/are inserted into the organism to a regulatory sequence that enhances the expression either at the transcriptional or the translational level. In this context, one useful approach is to link the gene operably to a strong homologous or heterologous promoter which optionally is a regulatable promoter. Interesting promoters are tRNA and rRNA promoters including the PI and PII promoters and the purD promoter from *Lactococcus lactis* subspecies *lactis* as described in WO 94/16086 to which there is referred.

A regulatable promoter regulating the expression of the gene coding for an NAD$^+$ regenerating enzyme can suitably be regulated by a factor selected from pH, the growth temperature, a temperature shift eliciting the expression of heat chock genes, the composition of the growth medium including the ionic strength/NaCl content and the presence/absence of purine nucleotide precursors, and the growth phase/growth rate of the bacterium.

It is also possible to obtain a helper organism having an increased NAD$^+$ regenerating activity by altering the structure of the enzyme e.g. by modifying the coding sequence or post-translationally by methods which are known per se.

In the present context, an example of a suitable NAD$^+$ regenerating enzyme is the NADH oxidase encoded by the nox gene.

In accordance with the present method, the helper organism capable of overexpressing a NAD$^+$ regenerating enzyme includes an organism wherein the enzyme catalyses the reduction of $O_2$ to $H_2O$ or $H_2O_2$, e.g. the enzyme having the sequence SEQ ID NO:2 as shown below. In useful embodiments the helper organism is an Ldh$^-$ strain.

As it is described above, lactic acid bacterial strains that are defective in their pyruvate metabolism include strains that are capable of reducing the amount of oxygen in a medium. It has been found that such strains, when used alone, i.e. without the concomitant addition of a starter culture strain, can improve the shelf-life of edible products, Accordingly, it is another objective of the invention to provide a method of improving the shelf life and/or the quality of an edible product, comprising adding to the product a lactic acid bacterial strain that is defective in its pyruvate metabolism as it is defined above. As used herein the term "shelf life" indicates the period of time in which the edible product is acceptable for consumption. In one useful embodiment, the lactic acid bacterial strains is one that has a reduced production of lactic acid including a strain that essentially does not produce lactic acid.

In accordance with the invention, a lactic acid bacterial strain that is useful for improving the shelf-life of edible products includes a strain as described above in which a gene coding for an enzyme that is capable of regenerating NAD[30] including the above NADH oxidases is overexpressed.

The above shelf-life improving effect can be obtained in a variety of edible product components or ingredients such as milk including non-pasteurized (raw) milk, meat, flour dough, wine and plant materials, such as vegetables, fruits or fodder crops. As used herein, the term "milk" is intended to mean any type of milk or milk component including e.g. cow's milk, human milk, buffalo milk, goat's milk, sheep's milk, dairy products made from such milk, or whey.

The rate at which the above lactic acid bacterial culture removes oxygen is dependent on the conditions of the medium, e.g. the temperature. With temperatures in the edible product components or ingredients often being lower than room temperature, such as below 10° C., e.g. below 5° C., the rate of which oxygen is removed may be as low as 1% per hour and still have an impact on the shelf life and/or quality of the edible product.

When used in accordance with the above method the non-acidifying lactic acid bacterial culture is preferably mixed with the edible product at the production site. Thus, as an example, when the edible product is non-pasteurized, raw milk the lactic acid bacterial culture can be added on the dairy farm to the milk subsequent to milking. Conveniently, the culture is added to the fresh milk in a cooling tank at the dairy farm or to a storage tank at a dairy plant.

In accordance with the method of the present invention it is also possible to achieve an enhancement of the biomass yield during starter culture production within a given period of time. Thus, this effect can be obtained when the volume of the starter culture is increased stepwise, which is also referred to in the art as "bulk starter systems".

As mentioned above, the invention provides in a further aspect a starter culture composition comprising at least one strain of a lactic acid bacterium and a lactic acid bacterial helper organism as described above that is defective in its pyruvate metabolism as also described above, including a helper organism that has a reduced production of lactic acid such as a strain that essentially does not produce lactic acid.

Typically, such compositions comprise the bacteria in a concentrated form including frozen, dried or freeze-dried concentrates typically having a concentration of viable cells which is at least $10^5$ CFU per gram of the composition, such as at least $10^6$ CFU/g including at least $10^7$ CFU/g, e.g. at least $10^8$ CPU/g, e.g. at least $10^{10}$ CFU/g, such as at least $10^{11}$ CFU/g, e.g. at least $10^{12}$ CFU/g, such as at least $10^{13}$ CFU/g of the composition. The composition may as further components contain cryoprotectants and/or conventional additives including nutrients such as yeast extract, sugars and vitamins.

In accordance with the invention there is also provided a lactic acid bacterium that is defective in at least one enzyme involved in the pyruvate metabolism as it is described above and in which a gene capable of regenerating $NAD^+$ is overexpressed, including a gene coding for an enzyme catalyzing the reduction of $O_2$ to $H_2O$ or $H_2O_2$ such as an $NADH:H_2O$ oxidase including the enzyme having the sequence SEQ ID NO:2.

As mentioned above, the invention also provides an isolated DNA fragment derived from a lactic acid bacterium comprising a gene coding for a polypeptide having $NADH:H_2O$ oxidase activity such as a DNA fragment which is selected from the group consisting of the sequence shown in SEQ NO ID:1 and a variant or derivative hereof which is at least 50% e.g. at least 60% including at least 70% identical with said sequence, and a recombinant DNA molecule comprising such a, DNA fragment. In the present context, the expression "variant or derivative" refers to any modification, including mutations, of the DNA sequence of the above specific sequence including substitution, addition or deletion of one or more nucleotides.

Figure 2:
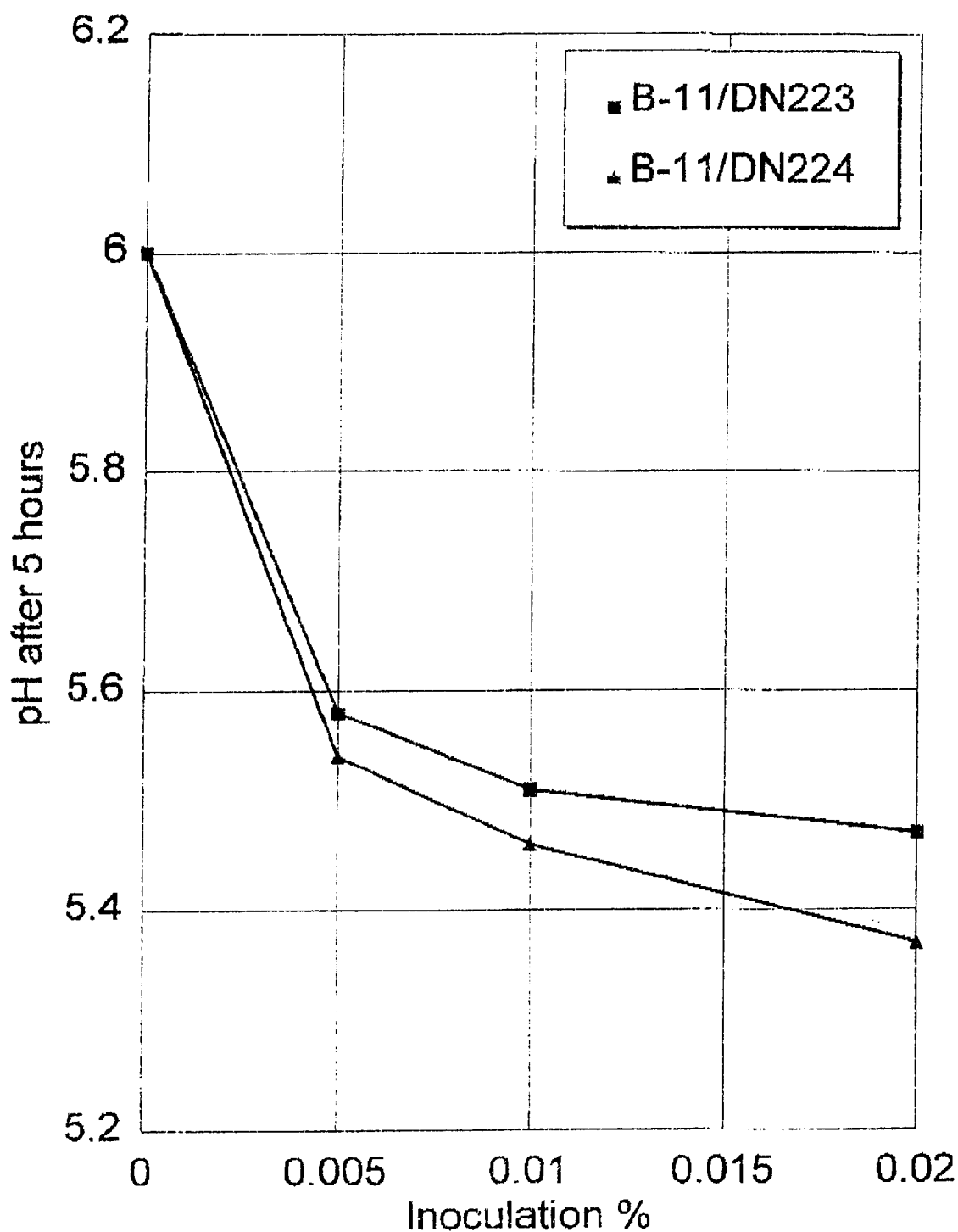
Figure 3:
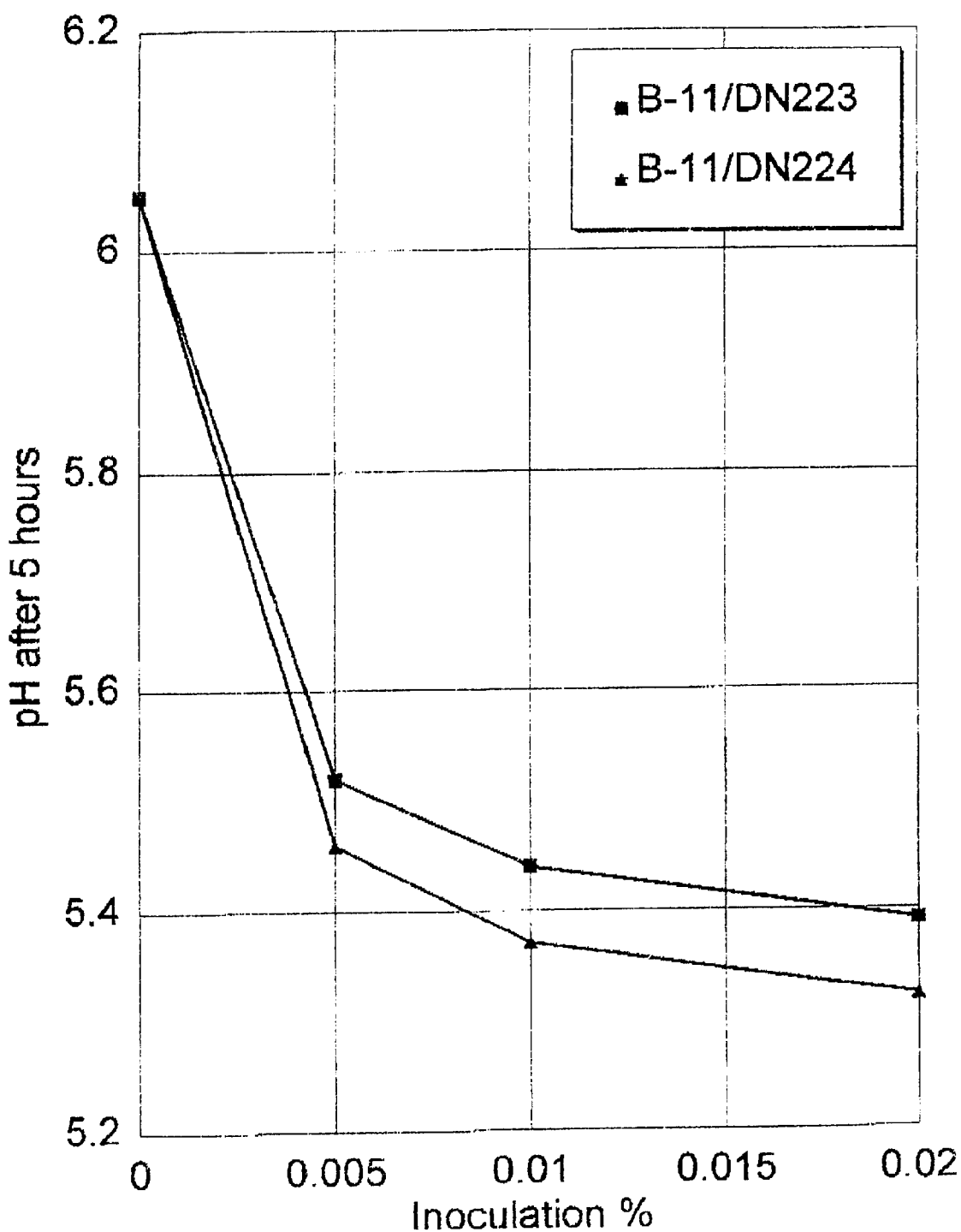
Figure 4:
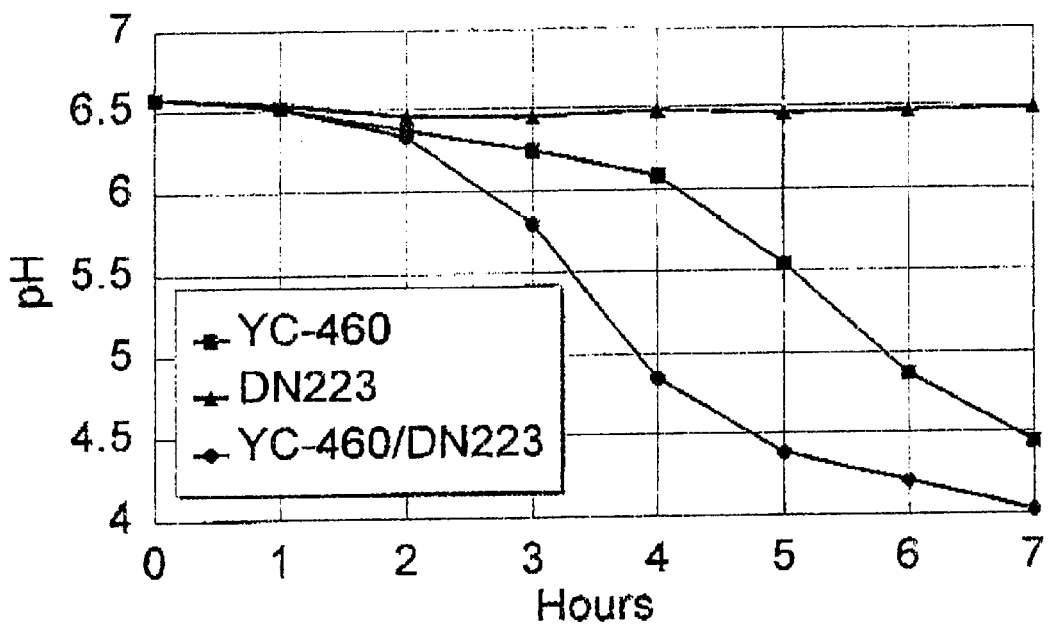
Figure 5:
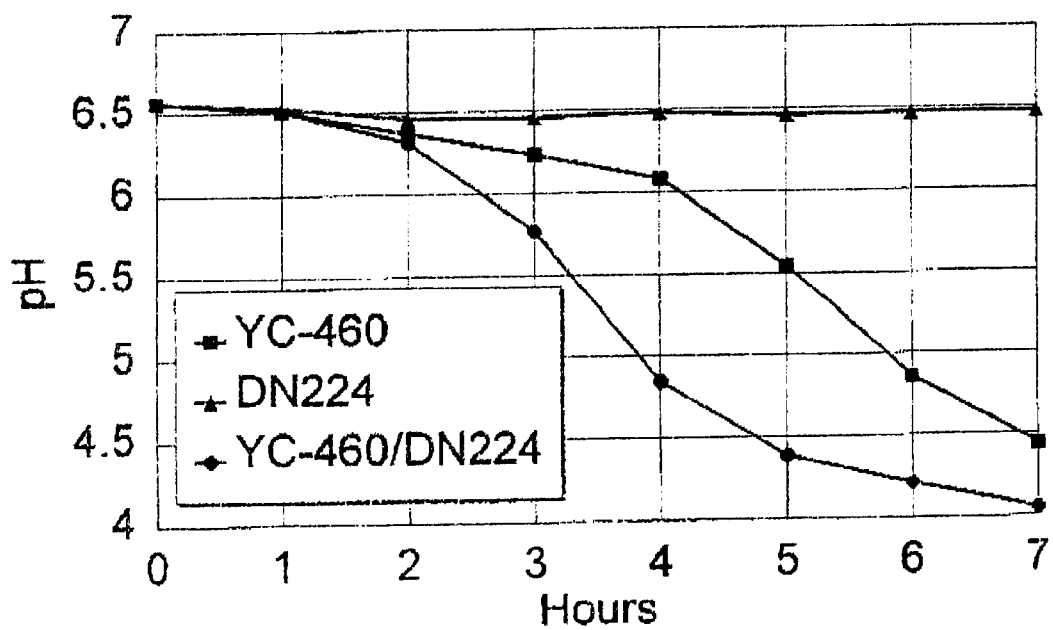
Figure 6A:
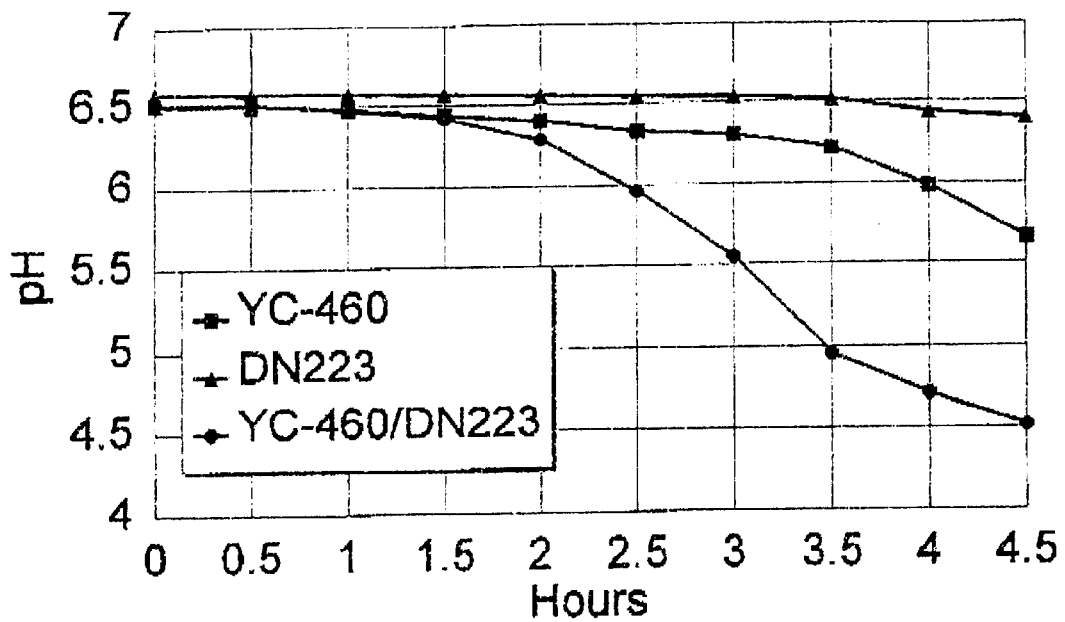
Figure 6B:
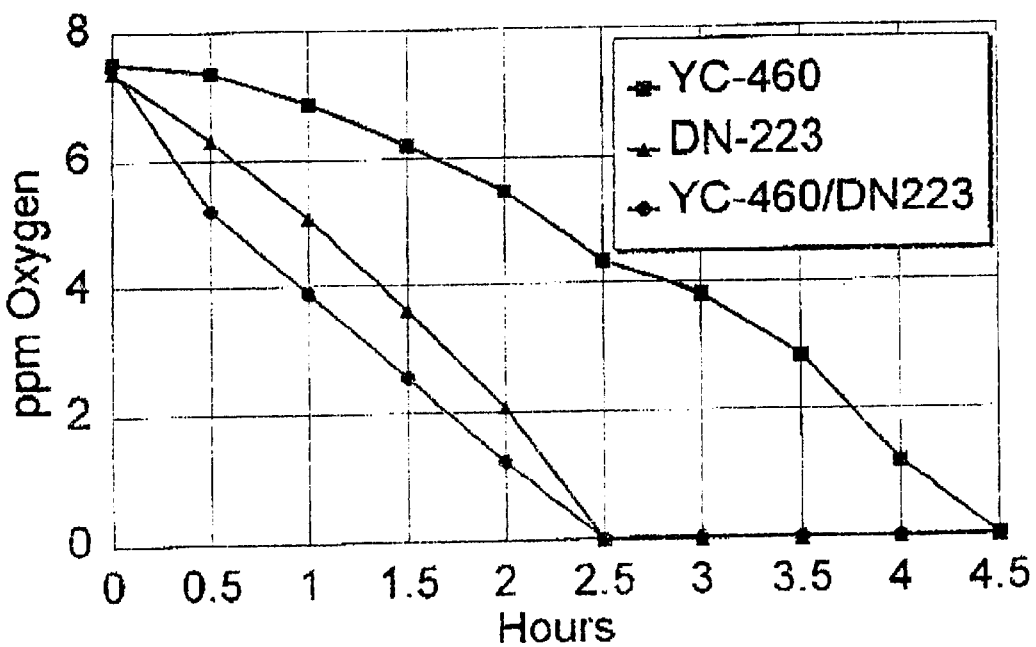
Figure 7A:
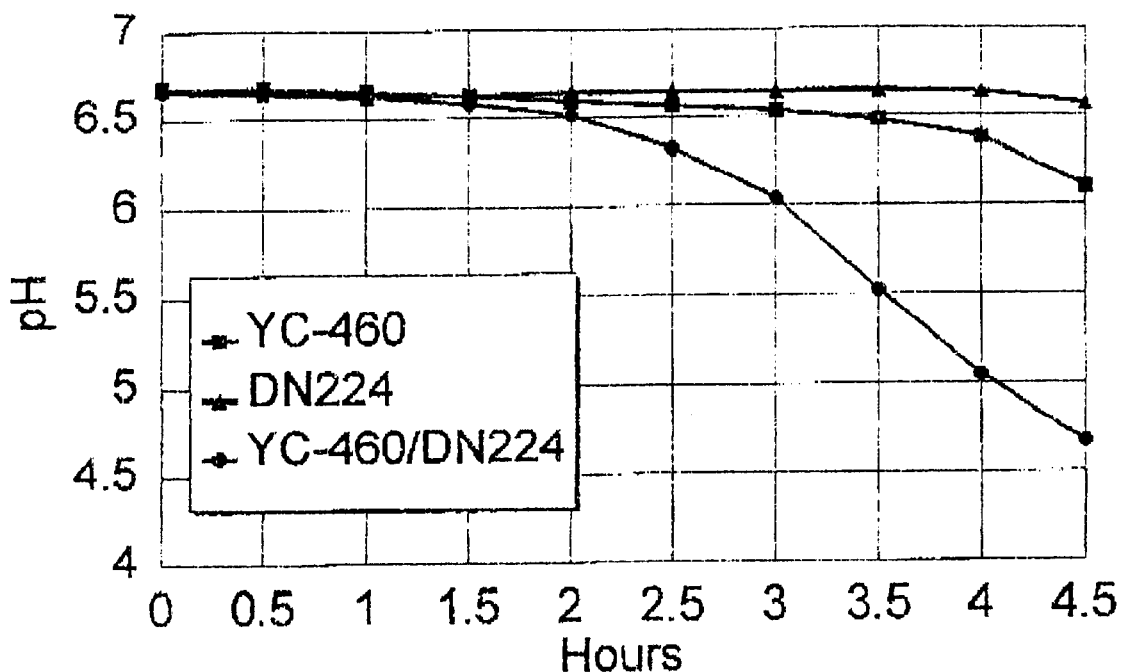
Figure 7B:
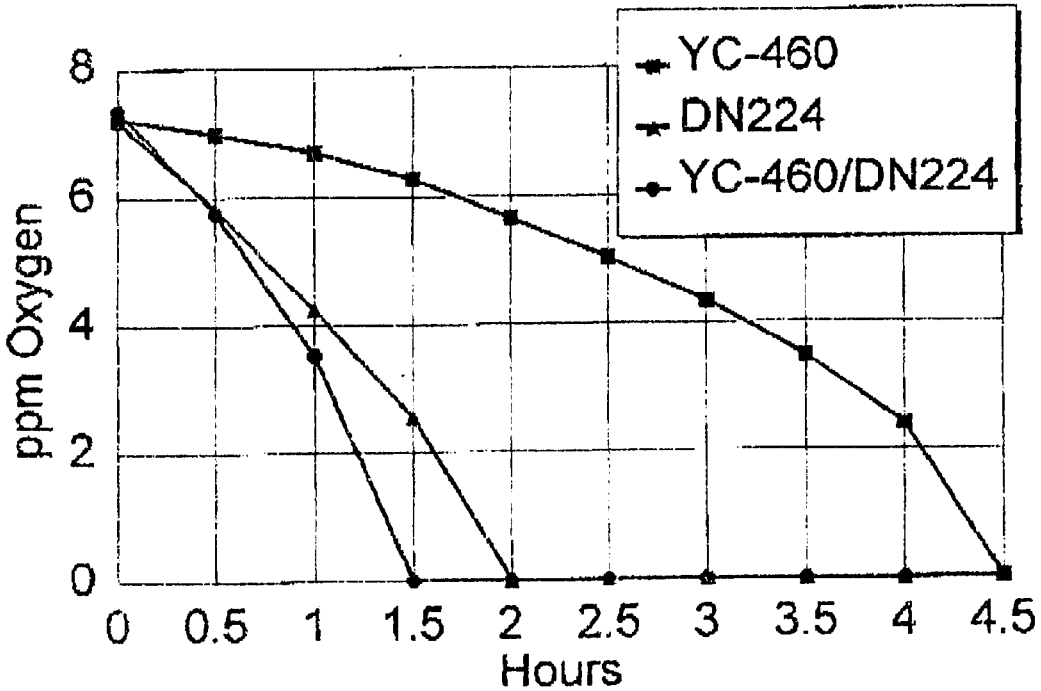
Figure 8A:
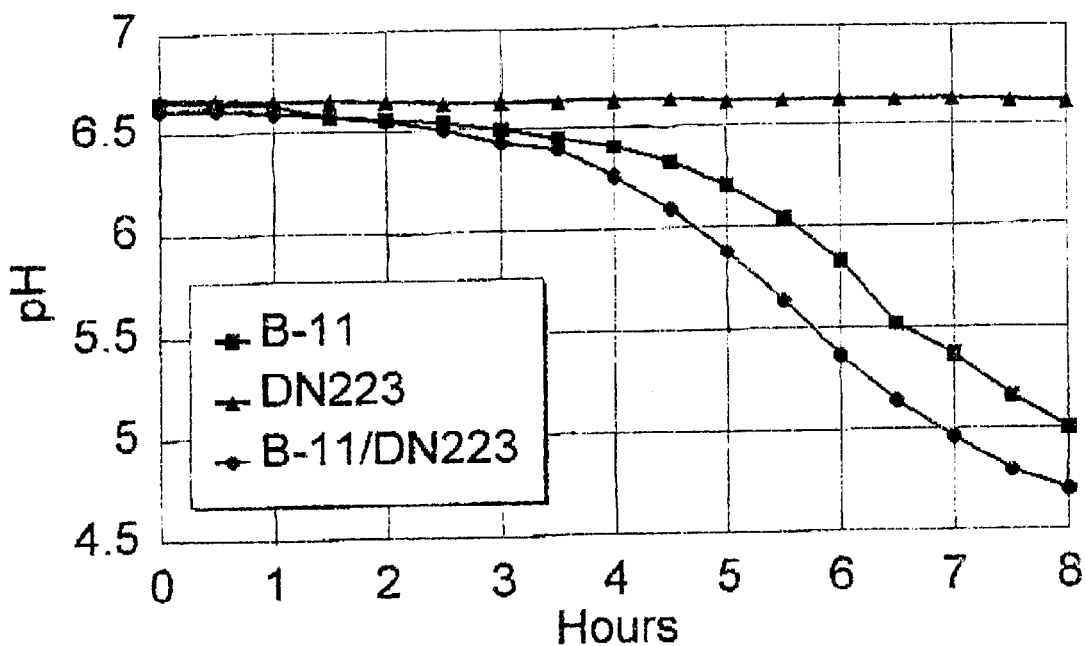
Figure 8B:
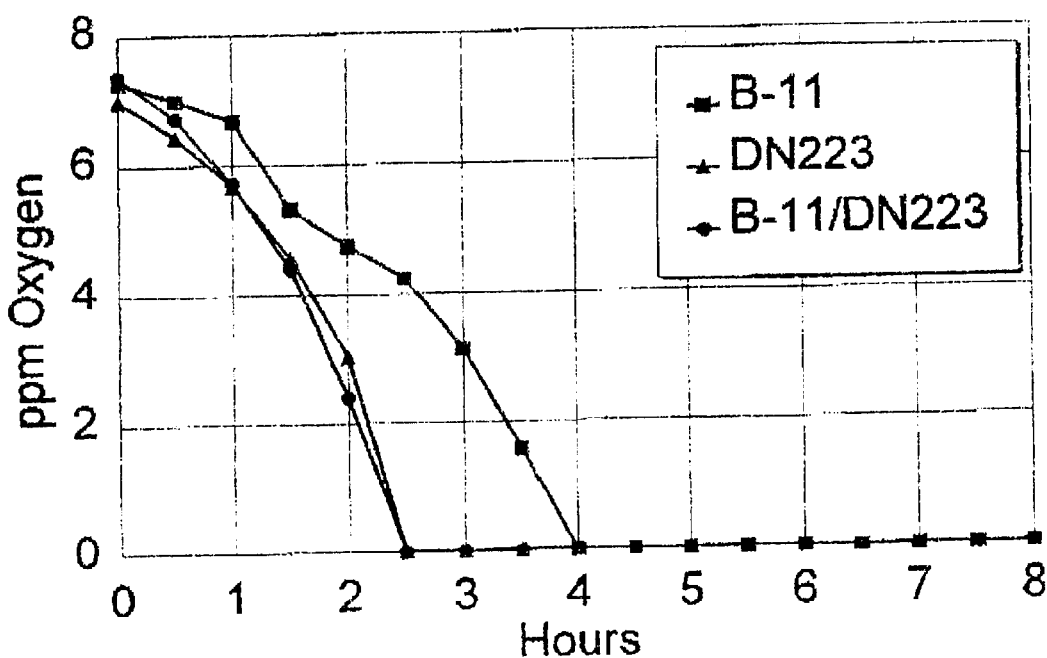
Figure 9A:
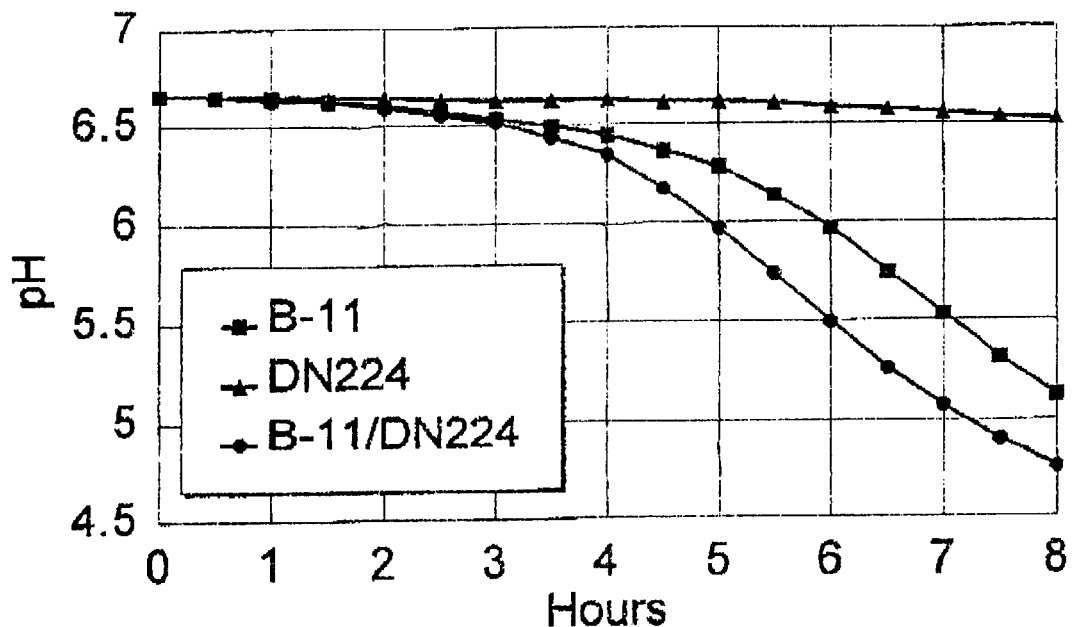
Figure 9B:
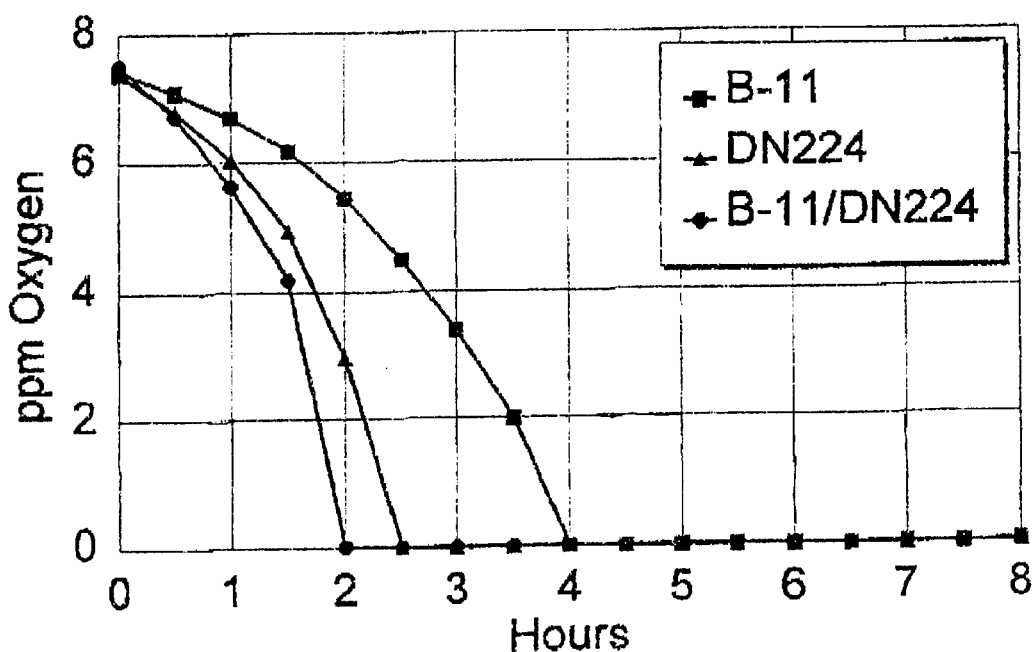

The invention is further illustrated in the following reference examples, examples and the drawing wherein:

FIG. 1 illustrates the effect on the acidification rates of the mesophilic lactic acid bacterial starter culture B-11 when cultivated in low pasteurized whole milk at 30° C. alone (0.01 wt %) and in association with the *Lactococcus lactis* subs. *lactis* strain DN223 and DN224, respectively, at the following concentrations: 0.005 wt %, 0.01 wt % to 0.02 wt %, FIG. 2 illustrates the effect on the acidification rates of the mesophilic lactic acid bacterial starter culture B-11 when cultivated in low pasteurized ecological whole milk at 30° C. alone (0.01 wt %) and in association with the *Lactococcus lactis* subs. *lactis* strain DN223 and DN224, respectively, at the following concentrations: 0.005 wt %, 0.01 wt % to 0.02 wt %, FIG. 3 illustrates the effect on the acidification rates of the mesophilic lactic acid bacterial starter culture B-11 when cultivated in high pasteurized skimmed milk at 30° C. alone (0.01 wt %) and in association with the *Lactococcus lactis* subs. *lactis* strain DN223 and DN224, respectively, at the following concentrations: 0.005 wt %, 0.01 wt % to 0.02 wt %, FIG. 4 illustrates the acidification of low pasteurized whole milk inoculated with the thermophilic lactic acid bacterial starter yoghurt culture YC-460 (0.02 wt %), the helper organism DN223 (0.003 wt %) and YC-460 (0.02 wt %) in association with DN223 (0.003 wt %), respectively, FIG. 5 illustrates the acidification of low pasteurized ecological whole milk inoculated with the thermophilic lactic acid bacterial starter yoghurt culture YC-460 (0.02 wt %), the helper organism DN224 (0.003 wt %) and YC-460 (0.02 wt %) in association with DN224 (0.003 wt %), respectively, FIG. 6A illustrates the acidification of low pasteurized ecological whole milk inoculated with the thermophilic lactic acid bacterial starter Yoghurt culture YC-460 (0.02 wt %), the helper organism DN223 (0.003 wt %) and YC-460 (0.02 wt %) in association with DN223 (0.003 wt %), respectively, FIG. 6B illustrates the effect on the oxygen concentration of low pasteurized ecological whole milk inoculated with the thermophilic lactic acid bacterial starter yoghurt culture YC-460 (0.02 wt %), the helper organism DN223 (0.003 wt %) and YC-460 (0.02 wt %) in association with DN223 (0.003 wt %), respectively, FIG. 7A illustrates the acidification of low pasteurized ecological whole milk inoculated with the thermophilic lactic acid bacterial starter yoghurt culture YC-460 (0.02 wt %), the helper organism DN224 (0.003 wt %) and YC-460 (0.02 wt %) in association with DN224 (0.003 wt %), respectively, FIG. 7B illustrates the effect on the oxygen concentration of low pasteurized ecological whole milk inoculated with the thermophilic lactic acid bacterial starter yoghurt culture YC-460 (0.02 wt %), the helper organism DN224 (0.003 wt %) and YC-460 (0.02 wt %) in association with DN224 (0.003 wt %), respectively, FIG. 8A illustrates the acidification of low pasteurized ecological whole milk inoculated with the mesophilic lactic acid bacterial starter culture B-11 (0.01 wt %), DN223 (0.0015 wt %) and B-11 (0.01 wt %) in association with DN223 (0.0015 wt %), FIG. 8B illustrates the effect of the oxygen concentration of low pasteurized ecological whole milk inoculated with the mesophilic lactic acid bacterial starter culture B-11 (0.01 wt %), DN223 (0.0015 wt %) and B-11 (0.01 wt %) in association with DN223 (0.0015 wt %), FIG. 9A illustrates the acidification of low pasteurized ecological whole milk inoculated with the mesophilic lactic acid bacterial starter culture B-11 (0.01 wt %), DN224 (0.0015 wt %) and B-11 (0.01 wt %) in association with DN224 (0.0015 wt %), FIG. 9B illustrates the effect of the oxygen concentration of low pasteurized ecological whole milk inoculated with the mesophilic lactic acid bacterial starter culture B-11 (0.01 wt %), DN224 (0.0015 wt %) and B-11 (0.01 wt %) in association with DN224 (0.0015 wt %).

REFERENCE EXAMPLES

Materials and Methods

1. Bacterial Strains, Media and Growth Conditions

The following lactic acid bacterial strains were used in the reference examples: *Lactococcus lactis* subspecies *lactis* strains 1FHCY-1, MG1363 and CHCC373 (Chr. Hansen Culture Collection) and *Lactococcus lactis* subspecies *lactis* biovar *diacetylactis* DB1341.

As growth media were used: (i) M17 medium (Terzaghi at al. 1975); (ii) the defined phosphate-buffered DN-medium (Dickely et al. 1995) with or without sodium acetate (DN or DN-Ac, respectively). The DN-medium does not contain lipoic acid, but was supplemented with NaFormate at a concentration of 0.6%; and (iii) reconstituted skim milk, RSM containing 9.5% low heat skim milk powder (Milex 240 lh, MD Foods, Denmark).

The strains were cultivated at 30° C. and growth was monitored by measuring the optical density (OD) at 600 nm and/or pH. Anaerobic conditions for growth on agar plates were obtained by incubation in a sealed container using the Anaerocult® A system (Merck, Darmstadt, Germany). In the following, anaerobic growth conditions for cultures in liquid media means cultivation without shaking and aerobic cultivation means growth under shaking.

2. Mutagenesis of *L. lactis*

A single colony of *L. lactis* was inoculated in 10 ml DN-medium and incubated for 16 hours under vigorous shaking. To the outgrown culture 150 µl of ethyl methane sulphonate (EMS, Sigma) was added and the mixture was incubated further under shaking. After 2 hours, 10 tubes each containing 2 ml DN-medium were each inoculated with 0.2 ml of the mutagenized culture. The tubes were incubated until the following day under shaking for phenotypic expression. Sterile glycerol was added to a final concentration of 15% (v/v) and the cultures were stored at −70° C. until use.

3. Determination of Lactate Dehydrogenase Activity

A single colony of *L. lactis* was inoculated in 10 ml M17 medium and cultivated overnight. After cooling for 15 min on ice, the cells were harvested by centrifugation at 7000 rpm for 5 min. at 4° C., washed in 5 ml ice-cold Ldh assay buffer (50 mM Tris-Acetate pH 6.0, 0.5 mM Fructose-1,6-diphosphate) and resuspended in 1 ml ice-cold Ldh assay buffer. The resuspended cells were transferred to a 5 ml glass tube and sonicated on Ice using a Branson Sonifier 250 at the following parameters: timer, 4 min.; duty cycle 25%; output 4. Subsequent to the sonication, the content of the tube was transferred to an ice-cold Eppendorf tube and centrifuged at 15.000×g for 5 min. at 4° C. The supernatant was transferred to a new ice-cold Eppendorf tube. The Ldh specific activity of the cell-free extract was measured at 25° C. in the following manner: 5 µl of cell-free extract was added to 495 µl Ldh assay buffer containing 0.2 mM NADH and 25 mM pyruvate. As control, an assay without pyruvate was used. The conversion of NADH to $NAD^+$ was followed spectrophotometrically over time at 340 nm using a to the conversion of 1 µmol. One unit corresponds The specific activity is expressed in units/mg protein. For measuring the protein concentration of the cell-free extract, the Bicinchoninic acid (BCA) assay (Pierce, Rockford, U.S.A.) was used with Albumin Standard (Pierce) as protein standard.

Reference Example 1

Acetate Requirement for Growth of *L. lactis*

Initially, the *L. lactis* subspecies *lactis* strains 1FHCY-1 and MG1363 were tested for growth on DN-medium with (DN) or without (DN-Ac) acetate, respectively.

The above mentioned s+rains were streaked onto DN and DN-Ac agar plates, respectively. The plates were incubated for 24 hours under anaerobic and aerobic conditions, respectively. The results are summarized in Table 1 below:

TABLE 1

| Acetate requirement of 1FHCY-1 and MG1363 | | | | |
|---|---|---|---|---|
| | Aerobic | | Anaerobic | |
| | +Ac | −Ac | +Ac | −Ac |
| 1FHCY-1 | +++ | − | +++ | +++ |
| MG1363 | +++ | − | +++ | +++ |

+++: colony size 0.6 1 mm;
−: no growth after prolonged incubation

The tested *L. lactis* strains have an absolute requirement for acetate under aerobic growth conditions.

The wild-type strain *Lactococcus lactis* subspecies *lactis* CHCC373 was selected from the culture collection of Chr. Hansen A/S, Hørsholm, Denmark and tested for its growth requirement for acetate under aerobic and anaerobic conditions respectively by streaking a liquid culture of the strain onto a series of DN-medium plates containing increasing concentrations of sodium acetate in the range of from 0 to 0.2% (w/v).

Under aerobic conditions weak growth was observed at 0.01% sodium acetate and at 0.02% full growth was observed. No growth was observed at concentrations below 0.005% sodium acetate. Under anaerobic conditions full growth was observed at 0–0.2% sodium acetate.

In the following experiments, DN-medium with 0.1% sodium acetate (DN) or not containing sodium acetate (DN-Ac) was used.

Reference Example 2

Isolation of Pfl Defective Mutants of *Lactococcus lactis* Subspecies *lactis* CHCC373 and *Lactococcus lactis* Subspecies *lactis* biovar *diacetylactis* DB1341 and Characterization Hereof 2.1. Isolation of Mutants Mutagenized stocks of the strains CHCC373 and DE1341 were prepared as described above and plated in dilutions onto DN-medium agar plates which were incubated aerobically for 24 to 48 hours. From these plates 980 colonies of each strain were selected and streaked onto DN and DN-Ac agar plates, respectively and these plates were incubated for 24 hours under anaerobic conditions. Two strains designated DN220 and DN221, respectively from the mutagenized CHCC373 strain and one strain designated DN227 from the mutagenized DB1341 strain which were unable to grow in the absence of acetate under anaerobic conditions were selected. Chromosomal DNA was isolated from DN220, DN221 and CHCC373, respectively and digested with EcoRI, and the fragment patterns were compared using agarose gel electrophoresis. The fragment patterns showed that both DN220 and DN221 originated from CHCC373. DN221 was selected for further experiments.

2.2 Growth of DN221 in M17 Medium and RSM

CHCC373 and DN221 were inoculated in M17 and the cultures were incubated under aerobic and anaerobic conditions, respectively. Under aerobic growth conditions, DN221 and CHCC373 did grow equally well as judged by the $OD_{600}$ and the pH. However, the growth rate of DN221 in M17 under anaerobic conditions was considerably lower than that of CHCC373 and it declined at a lower cell mass. These results showed that absence of acetate in M17 was not the reason for the slower growth rate of the selected mutant strain but indicated that an essential characteristic necessary for anaerobic growth is lacking in DN221 as compared to CHCC373. These results are consistent with the assumption that DN221 has a defect in its Pfl activity resulting in a requirement for acetate and a lower growth rate under anaerobic conditions as compared to CHCC373.

Reference Example 3
Isolation of Pfl and Ldh Defective Mutants

A stock of DN221 was mutagenized as described above under Materials and Methods, and the mutagenized cells were plated in dilutions onto DN-medium agar plates which were incubated aerobically for 24–48 hours. From theses plates, 980 colonies were selected and each colony was streaked onto two DN plates and incubated 24 hours under anaerobic and aerobic conditions, respectively. Two strains (DN222 and DN223) which were unable to grow under anaerobic conditions were selected.

Chromosomal DNA was isolated from DN222, DN223 and CHCC373, respectively and digested with EcoRI. The fragment patterns were compared using agarose gel electrophoresis. The fragment patterns showed that both DN222 and DN223 originate from. CHCC373.

A sample of DN222 and DN223, respectively was deposited with Deutsche Sammlung von Mikroorganismen und Zellkulturen GmbH, Mascheroder Weg 1b, D-38124 Braunschweig, Germany on Jun. 26, 1996 under the respective accession Nos. DSM 11035 and DSM 11036.

Reference Example 4
Isolating of Spontaneous Mutants of DN223

A liquid culture was made from a single colony of DN223 and incubated under aerobic conditions overnight. Approximately $10^8$ cells were transferred to DN-medium agar plates which were incubated under anaerobic conditions. Three strains designated DN224, DN225 and DN226 were isolated based on their ability to grow under anaerobic conditions. The three strains are all mutants or variants of DN223 having regained the ability to convert NADH to $NAD^+$ under anaerobic conditions either by mutations in secondary systems to Ldh and Pfl or by reversion of the Pfl or the Ldh defect.

Chromosomal DNA was isolated from DN224, DN225, DN226 and CHCC373, respectively and digested with EcoRI. The fragment patterns were compared using agarose gel electrophoresis. The fragment patterns showed that DN224, DN225 and DN226 all originate from CHCC373.

A sample of DN224, DN225 and DN226, respectively was deposited with Deutsche Sammlung von Mikroorganismen und Zellkulturen GmbH, Mascheroder Weg 1b, D-38124 Braunschweig, Germany on Jun. 26, 1996 under the respective accession Nos. DSM 11037, DSM 11038 and DSM 11039.

EXAMPLES
Materials and Methods

The following frozen concentrates of lactic acid bacterial strains were used as helper organisms throughout the examples: Laxtococcus lactis subspecies lactis strains DN223 which is pyruvate formate lyase (Pfl) and lactate dehydrogenase (Ldh) defective and DN224 which is Ldh defective. The cultures were produced according to procedures known in the art and concentrated 20 times before freezing. The total cell counts of the frozen concentrates were about $3\times10^{11}$ CFU/ml.

Example 1
The Effect of Helper Organisms on the Acidification Rate of Mesophilic Dairy Starter Cultures in Low Pasteurized Milk A frozen direct vat set (F-DVS) concentrate of a mesophilic culture commercially available from Chr. Hansen A/S, Hørsholm, Denmark, was cultured alone and in association with the above helper organisms. The mesophilic starter culture used was designated CH-N 19.

CH-N 19 is a starter culture with a total cell count of at least $1\times10^{10}$ CFU/g containing a mixture of Lactococcus lactis subs. cremoris, Lactococcus lactis subs. lactis, Leuconostoc mesenteroides subs. cremoris and Lactococcus lactis subs. diacetylactis.

CH-N 19 was used at an inoculation level of 0.01 wt %. The helper organisms were inoculated at a level of 0.001 wt %. The experiments were performed in low pasteurized whole milk at 30° C. with registration of pH at 1 hour intervals for 6 hours.

The pH development in low pasteurized whole milk inoculated with CH-N 19 alone and CH-N 19 in association with DN223 and DN224, respectively, is shown in Table 1.1 below.

TABLE 1.1

The development in pH in milk inoculated with
CH-N 19 alone and in association with DN223 and DN224

| Hours from | pH | | |
|---|---|---|---|
| inoculation | CH-N 19 | CH-N 19 + DN223 | CH-N 19 + DN224 |
| 3 | 6.53 | 6.52 | 6.51 |
| 4 | 6.40 | 6.36 | 6.37 |
| 5 | 6.16 | 6.04 | 6.02 |
| 6 | 5.80 | 5.64 | 5.60 |

When cultivated in association with this mesophilic culture the effect of the helper organisms DN223 and DN224 on the acidification rate after 5 hours of cultivation was a ΔpH of 0.12 and 0.14, respectively. The effect of the helper organisms was further increased after 6 hours of cultivation to a ΔpH of 0.16 and 0.20 pH units, respectively, i.e. pH 5.8 was reached 24 and 26 minutes faster when CH-N 19 was cultivated in association with DN223 and DN224, respectively, than when cultivated alone.

From these results it is clear that the acidification rate of the tested mesophilic dairy cultures can be enhanced by cultivation in association with helper organisms such as DN223 and DN224, the helper organisms being used in a concentration of about $3 \times 10^6$ CFU/g milk and the mesophilic culture being used at a concentration of about $1 \times 10^6$ CFU/g milk. A larger effect on enhancement of acidification rate was observed with DN224 as compared to DN223 under equivalent experimental conditions.

Example 2
The Effect of Helper Organisms on the Acidification Rate of Thermophilic Lactic Acid Bacterial Starter Cultures Three F-DVS concentrates of thermophilic lactic acid bacterial starter cultures commercially available from Chr. Hansen were cultivated alone (negative control) and in association with DN223 and DN224, respectively. The thermophilic cultures used are designated TCC-20, YC-460 and YC-470, respectively.

TCC-20 is a thermophilic starter culture with a total cell count of at least $1 \times 10^{10}$ CFU/g containing *Streptococcus thermophilus* and *Lactobacillus helveticus*. The culture is primarily applied in the production of cheese, e.g. Swiss cheese types, Italian cheese types, Mozzarella and Pizza cheese types.

YC-460 and YC-470 are both mixed strain cultures containing *Streptococcus thermophilus* and *Lactobacillus delbrueckii* subs. *bulgaricus*. The cultures are primarily used in the production of yoghurt. Both cultures give a high flavour level in yoghurt and YC-460 results in a medium viscosity and YC-470 in a high viscosity of the yoghurt.

The TCC-20 culture was used at an inoculation level of 0.01 wt % and at a temperature of 37° C. YC-460 and YC-470 was used at an inoculation level of 0.02 wt % and at a temperature of 43° C. The helper organisms were inoculated at a level of 0.001 wt %. The weight ratio between the starter cultures and DN223 and DN224, respectively, was 1:10 in the case of TCC-20 and 1:20 in the case of the Yoghurt Cultures. All experiments were performed in 200 ml low pasteurized whole milk with registration of pH for 5 hours at 1 hour intervals.

2.1 Results Obtained with the Dairy Culture TCC-20.

The acidification of low pasteurized whole milk inoculated with TCC-20 alone and in association with DN223 and DN224, respectively, is shown in Table 2.1 below.

TABLE 2.1

The development of pH in milk inoculated with TCC-20 alone and in association with DN223 and DN224, respectively.

| Hours after | pH | | |
|---|---|---|---|
| Inoculation | TCC-20 | TCC-20 + DN223 | TCC-20 + DN224 |
| 2 | 6.50 | 6.52 | 6.51 |
| 3 | 6.53 | 6.48 | 6.47 |
| 4 | 6.28 | 6.08 | 5.95 |
| 5 | 6.15 | 5.48 | 5.34 |

After only 4 hours the results of cultivating TCC-20 in association with DN223 and DN224, respectively, was a ΔpH of 0.20 and 0.33, respectively. After 5 hours of cultivation the effect of DN223 and DN224 had increased to a ΔpH of 0.67 and 0.81, respectively. A pH of 6.2 in the milk was reached 55 and 66 minutes faster when the TCC-20 culture was inoculated in association with DN223 and DN224, respectively, than when cultivated alone.

2.2 Results Obtained with the Dairy Starter Culture YC-470.

The development of pH in milk resulting from cultivating YC-470 alone and in association with DN223 and DN224, respectively, is shown in Table 2.2.

TABLE 2.2

The development of pH in milk inoculated with YC-470 alone and in association with DN223 and DN224, respectively.

| Hours after | pH | | |
|---|---|---|---|
| inoculation | YC-470 | YC-470 + DN223 | YC-470 + DN224 |
| 1 | 6.50 | 6.50 | 6.51 |
| 2 | 6.38 | 6.35 | 6.34 |
| 3 | 6.32 | 6.03 | 6.00 |
| 4 | 5.94 | 5.11 | 5.06 |
| 5 | 5.47 | 4.51 | 4.46 |

Also this culture benefited significantly from the presence of DN223 and DN224, The acidification rate after 3 hours was increased with a ΔpH of 0.29 and 0.32, respectively, after 4 hours with a ΔpH of 0.83 and 0.88, respectively, and further after 5 hours with ΔpH of 0.96 and 1.01.

The increase in acidification rate, expressed as the reduction of time required for the YC-470 culture to acidify the milk to a pH of 6.0 was 49 and 51 minutes, respectively, when the YC-470 culture was inoculated in association with DN223 and DN224, respectively, compared to being cultivated alone.

2.3 Results Obtained with the Dairy Starter Culture YC-460.

The development of pH in milk inoculated with YC-460 alone and in association with DN223 and DN224, respectively, is shown in Table 2.3 below.

TABLE 2.3

The development of pH in milk inoculated with YC-460 alone and in association with DN223 and DN224, respectively.

| Hours after | pH | | |
|---|---|---|---|
| inoculation | YC-460 | YC-460 + DN223 | YC-460 + DN224 |
| 1 | 6.53 | 6.52 | 6.52 |
| 2 | 6.43 | 6.42 | 6.42 |
| 3 | 6.43 | 6.18 | 6.12 |
| 4 | 6.14 | 5.23 | 5.14 |
| 5 | 5.87 | 4.53 | 4.45 |

When cultivated in association with the helper organisms DN223 and DN224 an effect on the acidification rate was seen as early as after 3 hours of cultivation with a ΔpH of 0.25 and 0.31, respectively. A more significant effect of cultivating YC-460 in association with the helper organisms DN223 and DN224, respectively, was observed after 4 hours with a ΔpH of 0.91 and 1.00, respectively. A further increased effect was observed after 5 hours with a ΔpH to 1.34 and 1.42 for DN223 and DN224, respectively.

The increase in acidification rate, expressed as the reduction of time required for the YC-460 culture to acidify the milk to a pH of 6.0 was 78 and 83 minutes, respectively, when the YC-460 culture was cultivated in combination with DN223 and DN224, respectively, as compared to the cultures being cultivated without helper organisms.

As with the mesophilic cultures, a larger effect was seen when cultivating the thermophilic starter cultures in association with DN224 rather than with DN223. The difference between the two helper organisms was not as pronounced when used in association with thermophilic cultures. The effect of the helper organisms as measured by the increased acidification rate was significantly greater when used in association with thermophilic cultures. Of the tested cultures the associative growth with DN223 and DN224, respectively, was of the largest benefit to the yoghurt cultures YC-460 and YC-470, the increase of acidification rate after 5 hours being about 1 pH unit with a weight ratio of 1:20 between the yoghurt cultures and DN223 and DN224, respectively. The two helper organisms were able to reduce significantly the time required to acidify the milk to a certain pH when inoculated at a level of 0.001 wt % of the substrate.

Example 3

The Effect of Helper Organisms on the Acidification of a Lactic Acid Bacterial Starter Culture Containing Both Mesophilic and Thermophilic Strains The effect of the helper organisms DN223 and DN224 on acidification rate in milk was determined for mixed starter cultures intended for the production of Dutch and continental cheese. These mixed starter cultures contains mesophilic and thermophilic lactic acid bacterial strains. The starter cultures were inoculated as frozen DVS. The following starter cultures were used:

YY-62 and YY-63 are starter cultures consisting of a mixture of both mesophilic and thermophilic lactic acid bacterial strains.

TH4 is a commercial starter culture containing a thermophilic lactic acid bacterial strain.

B-11 is a commercial mesophilic mixed starter culture containing strains of *Lactococcus lactis* subs. *cremoris*, *Lactococcus lactis* subs. *lactis, Leuconostoc mesenteroides* subs. *cremoris* and *Lactococcus lactis* subs. *diacetylactis*. The culture has a total cell count of at least $1 \times 10^{10}$ CFU/g. The starter culture has a content of *Leuconostoc mesenteroides* subs, *cremoris* in the range of 1–5% based on the total cell count and of *Lactococcus lactic* subs. *diacetylactis* in the range of 5–30% based on the total cell count.

The evaluation of the acidification rate was made by inoculation of the starter cultures into pasteurised whole milk. The temperature was controlled by an automatic temperature controller, generating a typical Danbo cheese temperature profile. The starter cultures were incubated at the levels indicated in the tables below. The milk had been stored overnight at 4–7° C. in bottles with loose lids, in order to ensure equal level of oxygen saturation ire all bottles.

The pH development was measured semi-continuously throughout the 16 hours of incubation by AAC hardware from Intab A/B. Acidification curves were generated by the software package Easyview version 3.2.0.4. The pH values measured after 5 and 6 hours incubation are shown in the tables below.

3.1 The Effect of Adding the Helper Organisms DN223 or DN224 to the Starter Culture YY-62.

The inoculation level of the starter culture YY-62 and/or helper organisms DN223 and DN224 is shown in Table 3.1:

TABLE 3.1

Inoculation level (wt % of milk) of YY-62, DN223 and DN224

| Culture | Culture | DN223/DN224 | Total inoc. |
|---|---|---|---|
| YY-62 | 0.0034% | 0% | 0.0034% |
| YY-62 + DN223 | 0.00331% | 0.0014% | 0.0048% |
| YY-62 + DN224 | 0.00338% | 0.0015% | 0.0049% |

The pH after 5 and 6 hours in pasteurized whole milk inoculated with the starter culture alone and in association with the helper organisms DN223 and DN224, respectively, is shown in Table 3.2:

TABLE 3.2 pH after 5 and 6 hours in pasteurised whole milk inoculated with YY-62 alone or in association with DN223 and DN224

| Culture | Unit | 5 hours | 6 hours |
|---|---|---|---|
| YY-62 | pH | 6.35 | 6.24 |
| YY-62 + DN223 | pH | 6.19 | 6.01 |
| YY-62 + DN224 | pH | 6.13 | 5.94 |
| Temp. bottle | ° C. | 31.18 | 26.2 |

3.2 The Effect of Adding DN223 or DN224 to the Starter Culture YY63.

The inoculation level of the starter culture YY-63 with or without the helper organisms DN223 or DN224 is shown in Table 3.3:

TABLE 3.3

Inoculation level (wt % of milk) of YY-63, DN223 and DN224

| Culture | Culture | DN223/DN224 | Total inoc. |
|---|---|---|---|
| YY-63 | 0.0034% | 0% | 0.0034% |
| YY-63 + DN223 | 0.00337% | 0.0017% | 0.0051% |
| YY-63 + DN224 | 0.00347% | 0.0015% | 0.0050% |

The pH after 5 and 6 hours in pasteurised whole milk inoculated with the starter culture alone and in association with the helper organisms DN223 and DN224, respectively, is shown in Table 3.4:

TABLE 3.4 pH after 5 and 6 hours in pasteurised whole milk inoculated with YY-62 alone or in association with DN223 or DN224

| Cultures | Unit | 5 hours | 6 hours |
|---|---|---|---|
| YY-63 | pH | 6.26 | 6.10 |
| YY-63 + DN223 | pH | 6.04 | 5.75 |
| YY-63 + DN224 | pH | 6.07 | 5.80 |
| Temp. bottle | ° C. | 31.05 | 26.06 |

3.3 The Effect of Adding the Helper Organisms DN223 or DN224 to the Starter Culture YY-43, a Mixture of Starter Culture B-11 and Starter Culture TH4.

The inoculation level of the starter culture YY-43, which is a mix-starter culture containing the starter culture B-11 and starter culture TH4, and/or helper organisms DN223 and DN224 is shown in Table 3.5.

TABLE 3.5

Inoculation level (% wt of milk) of YY-43, DN223 and DN224

| Culture | Culture | DN223/DN224 | Total inoc. |
|---|---|---|---|
| YY-43 | 0.0036% | 0% | 0.0036% |
| YY-43 + DN223 | 0.00345% | 0.0015% | 0.0050% |
| YY-43 + DN224 | 0.0034% | 0.0014% | 0.0049% |

The pH after 5 and 6 hours in pasteurised whole milk inoculated with the starter culture alone and in association with the helper organisms DN223 and DN224, respectively, is shown in Table 3.6:

TABLE 3.6 pH after 5 and 6 hours in pasteurised whole milk
inoculated with YY-62 alone or in association with DN223 and DN224

| Culture | Unit | 5 hours | 6 hours |
|---|---|---|---|
| YY-43 | pH | 6.17 | 5.97 |
| YY-43 + DN223 | pH | 6.03 | 5.78 |
| YY-43 + DN224 | pH | 6.03 | 5.81 |
| Temp. | ° C. | 30.85 | 25.83 |

3.6 Conclusions

A marked effect of the addition of helper organisms according to the invention on the acidification rate of three different lactic acid bacterial starter cultures has been demonstrated (3.1., 3.2 and 3.3). Thus, after 6 hours the pH was reduced by 0.19–0.35 pH units for the starter cultures YY-62, YY-63 and YY-43. This enhancement of the acidification rate of the starter cultures implies that a desired acidification of milk can be obtained by using 50% of the normal level of the starter culture to achieve the equivalent acidification when this reduced level of starter culture is supplemented with a helper organism of the invention.

Example 4

Dosage Response of the Helper Organisms 4.1 Effect of Increasing the Dosage of Helper Organisms on the Acidification of B-11 in Different Milk Substrates The effect of increasing the amount of helper organism on the acidification rate of a dairy starter culture was tested using the mesophilic culture designated B-11 cultivated in association with DN223 and DN224, respectively.

B-11 is a mesophilic starter culture as described in Example 3.

Three substrates were used: low pasteurized whole milk, low pasteurized ecological whole milk and high pasteurized skimmed milk. The inoculation level of the B-11 culture was 0.01 wt %. The helper organisms were tested at 4 different inoculation levels: 0 wt % 0.005 wt %, 0.01 wt % and 0.02 wt %, respectively. All experiments were performed at 30° C. and the pH of the substrate was measured after 5 hours of incubation.

The results for each of the above substrates are shown in FIGS. 1, 2 and 3, respectively. All three experiments showed that the acidification of the substrates was enhanced significantly when B-11 was cultivated in association with DN223 and DN224, respectively, the effect of DN224 in general being better than that of DN223. There was only observed minor deviations in the effect between the different milk substrates. In whole milk there was a large decrease in pH from 5.97 to 5.58 and 5.55 when B-11 was cultivated in association with 0.005 wt % of DN223 and DN-224, respectively. The decrease in pH was further enhanced when DN223 and DN224 was used at an inoculation level of 0.01 wt % resulting in a pH of 5.53 and 5.48, respectively, When the inoculation level of the helper organism was increased to 0.02 wt % no further increase in the acidification rate was observed.

When the starter culture B-11 was inoculated at 0.01 wt % and cultivated in association With DN223 and DN224, respectively, a larger effect was achieved with an amount of helper organism of about 0.005 wt %, the effect only to a smaller extent being dependent on the milk substrate.

4.2 The Effect of Increasing the Dosage of Helper Organisms on the Acidification Rate of YC-460 in Pasteurized Whole Milk The development of pH in 1000 ml low pasteurized whole milk inoculated with 0.02 wt % YC-460, 0.003 wt % DN223 and 0.02 wt % YC-460 in association with 0.003 wt % DN223 is shown in FIG. 4. Corresponding results obtained with the helper organism DN224 is shown in FIG. 5.

The time used to acidify the milk to pH 6.0 was reduced by about 92 and 96 minutes when YC-460 was cultivated in association with DN223 an DN224, respectively, as compared to being cultivated alone.

Compared to the results obtained in Example 2.3 an increase of acidification rate was seen when the inoculation level of the helper organism was increased from 0.001 wt % to 0.003 wt %. The time required for the YC-460 culture to acidity the milk to pH 6.0 was further reduced by 13–14 minutes when the amount of helper organism was increased from 0.001 wt % to 0.003 wt %.

A pH of 4.5 in the milk and this was reached after 6 hours and 52 minutes when the milk was inoculated with YC-460 alone and after 4 hours and 44 minutes and 4 hours and 45 minutes when inoculated with YC-460 in association with DN223 and DN224, respectively.

Example 5

The Effect of DN223 and DN224 on the Oxygen Concentration of Milk in Relation to the Acidification Rate of the Starter Cultures The development in pH and oxygen concentration was monitored when cultivating milk with starter cultures of both mesophilic and thermophilic types and with the starter cultures in association with DN223 and DN224, respectively. pH was measured using a Chemap pH-amplifier ad a Mettler Toledo HA 465-50-T-S-7 electrode and the oxygen concentration was measured using a Chemap $O_2$ amplifier and an Ingold $pO_2$ electrode. As negative controls milk was inoculated with DN223 and DS224, respectively. The cultivations were performed in 40 liter fermenters with moderate mixing and using 30 liter ecologicals low pasteurized whole milk as the substrate.

Four sets of experiments were performed in 3 parallel fermenters with the following additions of starter culture and/or helper organisms:

| Experiment A: | i) 0.02 wt % YC-460,<br>ii) 0.003 wt % DN223 and<br>iii) 0.02 wt % YC-460 in association with 0.003 wt % DN223. |
|---|---|
| Experiment B: | i) 0.02 wt % YC-460,<br>ii) 0.003 wt % DN224 and<br>iii) 0.02 wt % YC-460 in association with 0.003 wt % DN224. |
| Experiment C: | i) 0.01 wt % B-11,<br>ii) 0.0015 wt % DN223 and<br>iii) 0.01 wt % B-11, in association with 0.0015 wt % DN223. |
| Experiment D: | i) 0.01 wt % B-11,<br>ii) 0.0015 wt % DN224 and<br>iii) 0.01 wt % B-11 in association with 0.0015 wt % DN224. |

The temperature was kept at 43° C. when cultivating the thermophilic culture YC-460 and at 30° C. when cultivating the mesophilic culture B-11. The pH and oxygen concentration were measured and recorded at half hour intervals.

The results obtained in experiment A are shown in FIGS. 6A and 6B, respectively, and the results obtained in experiment B are shown in FIGS. 7A and 7B, respectively.

From FIGS. 6A and 6B it can be seen that where YC-460 was cultivated alone, the oxygen was consumed at a slow rate resulting in an oxygen-free medium after 4.5 hours. The acidification of the milk was very limited when the oxygen content of the milk was high and pH 6 was reached after 4 hours.

Inoculating the milk with DN223 resulted in a rapid decrease in the oxygen content of the milk, the oxygen being totally removed after 2.5 hours. Substantially no acidification of the milk was observed under these conditions.

Inoculating the milk with YC-460 in association with DN223 resulted in a rapid decrease of the oxygen concentration in the milk, the oxygen being totally removed after 2.5 hours. The acidification rate of the milk was slow at high oxygen concentrations in the milk, but accelerated at an earlier point than when YC-460 was inoculated alone, i.e. pH was below 6 after only 2.5 hours.

When comparing with the corresponding results shown in FIGS. 6A and 6B it is evident that the acidification of the milk by YC-460 was correlated to the oxygen concentration. The YC-460 starter culture was capable of removing the oxygen from the medium by itself but did it slowly. When the oxygen content was in the range of 0–3 ppm the acidification of the medium by YC-460 was significant. The presence of DN223 in association with YC-460 enhanced the removal of the oxygen and thereby decreased the time until onset of acidification. The more rapid onset of acidification was not due to acidification of the medium by DN223.

Similar results were obtained with associative cultivation of YC-460 and DN224, shown in FIGS. 7A and 7B. Inoculation of the milk with DN224 alone resulted in a fast decrease in the oxygen content of the milk, the medium being oxygen-free after only 1.5 hours. Substantially no acidification of the milk was observed.

The acidification of the milk by YC-460 resulted in a pH about 6 within 4.5–5 hours and this pH was obtained with the associative culture of YC-460 and DN224 after about only 3 hours.

Even though DN224 removes the oxygen in the medium more rapidly than does DN223 the improved acidification rate of YC-460 in association with DN224 was essentially the same as that obtained with DN223. This indicates that the oxygen concentration in the medium is one factor having an effect on the acidification of milk by thermophilic cultures.

The results of experiment C are shown in FIGS. 8A and 8B, and the results of experiment D are shown in FIGS. 9A and 9B.

From the figures it can be seen that inoculation of milk with 0.0015 wt % DN223 and DN224 resulted in the oxygen being totally removed after 2.5 hours for both helper organisms. This corresponds to the results obtained when the milk was inoculated with 0.003 wt % DN223. After 2 hours of incubation the higher inoculation level of DN223 had reduced the oxygen concentration to about 2 ppm whereas the lower inoculation level of both DN223 and DN224 resulted in an oxygen level of about 3 ppm. With 0.003 wt % DN224 the oxygen was totally removed after 2 hours of incubation and after 1.5 hours the oxygen concentration was about 2.5 ppm.

The results of associative cultivation of B-11 with DN223 and DN224, respectively, shows that the acidification rate of this culture was improved by the presence of the helper organisms. The improved acidification rates were almost the same where using DN223 and DN224. pH values of 5.88 and 5.97 obtained after 5 hours incubation with B-11 in association with DN223 and DN224, respectively, can be compared to 5.58 and 5.54 obtained in Example 3 with 0.005 wt % of DN223 and DN224, respectively. The effect of increasing the amount of helper organism from 0.0015 wt % to 0.005 wt % is thus a decrease in the pH after 5 hours from 5.88 to 5.58 with DN223 and from 5.97 to 5.54 with DN224.

From FIG. 8A it can be seen that a pH of 5.2 in the milk was reached after 7 hours and 24 minutes when the milk was inoculated with B-11 alone and after 6 hours and 22 minutes when inoculated with B-11 and DN223 in association. From FIG. 9A it can be seen that pH 5.2 was reached after 7 hours and 48 minutes when the milk was inoculated with B-11 alone and after 6 hours and 39 minutes when inoculated with B-11 in association with DN224.

The following bacterial strains have been deposited under the Budapest Treaty on Jun. 26, 1996 with the IDA Deutsche Sammlung von Mikroorganismen und Zellkulturen GmbH (DSM), Mascheroder Weg 1b, D-38124, Braunschweig, Federal Republic of Germany.

| Strain | Deposit No. |
| --- | --- |
| DN220 | DSM11033 |
| DN221 | DSM11034 |
| DN222 | DSM11035 |
| DN223 | DSM11036 |
| DN224 | DSM11037 |
| DN225 | DSM11038 |
| DN226 | DSM11039 |
| DN227 | DSM11040 |

These strains will be irrevocably, and without restriction or condition, released to the public upon the issuance of a U.S. patent on this application.

REFERENCES

1. Condon, S. 1987. Responses of lactic acid bacteria to oxygene. FEMS Microbiology Review, 46, 249–280.
2. Dickely, F., Nilsson, D., Hansen, E. B. and Johansen, E. 1995. Isolation of *Lactococcus lactis* nonsense suppressors and construction of a food-grade cloning vector. Molec. Microbiol., 15, 839–847.
3. Rajagopal, S. N. and Sandine, W. E. 1990. Associative growth and proteolysis of *Streptococcus thermophilus* and *Lactobacillus bulgaricus* in skim milk. J. Dairy Sci., 73, 894–899.
4. Suzuki, I., Kato, S. Kitada, T., Yano, N. and Morichi, T. 1986. Growth of *Lactobacillus bulgaricus* in milk. 1. Cell elongation and the role of formic acid in boiled milk. J. Dairy Sci., 69, 311–320.
5. Terzaghi, B. E. and Sandine, W. E. 1975. Improved medium for the lactic streptacocci and their bacteriophages. Appl. Microbiol., 29, 807–813.

What is claimed is:

1. A method of enhancing the growth rate and/or controlling the metabolic activity of a lactic acid bacterial strain, comprising cultivating the strain in association with a lactic acid bacterial helper organism that is defective in its pyruvate metabolism.

2. A method according to claim 1 wherein the cultivation of the lactic acid bacterial strain in association with the helper organism results in an enhancement of the acid production of the strain.

3. A method according to claim 2 wherein the cultivation results in a ΔpH of at least 0.05 after 3 hours or more of cultivation.

4. A method according to claim 1 wherein the strain is cultivated in a medium having an initial degree of oxygen saturation which is 10% or higher.

5. A method according to claim 4 wherein the medium has an initial degree of oxygen saturation which is 20% or higher.

6. A method according to claim 1 wherein the helper organism is capable of reducing the amount of oxygen present in the medium by at least 1% per hour.

7. A method according to claim 1, wherein the helper organism is a derivative of a lactic acid bacterium.

8. A method according to claim 7 wherein the helper organism essentially does not produce lactic acid.

9. A method according to claim 1 wherein the helper organism is defective in its ability to express at least one enzyme selected from the group consisting of pyruvate formate lyase, pyruvate dehydrogenase, lactate dehydrogenase, acetolactate synthetase, second acetolactate synthetase, acetolactate decarboxylase and diacetyl reductase.

10. A method according to claim 9 wherein the helper organism is *Lactococcus lactis* subs. *lactis* strain DN223 deposited under the accession No. DSM 11036.

11. A method according to claim 9 wherein the helper organism is *Lactococcus lactis* subs. *lactis* strain DN224 deposited under the accession No. DSM 11037.

12. A method according to claim 1 wherein the lactic acid bacterial strain is cultivated in a medium which is selected from the group consisting of milk, meat, flour dough, wine and a plant material.

13. A method according to claim 1 wherein the ratio between helper organism cells and cells of the lactic acid bacterial strain is in the range of 1000:1 to 1:1000.

14. A method according to claim 1 wherein a gene coding for an enzyme that is capable of regenerating $NAD^+$ is overexpressed in the helper organism.

15. A method according to claim 14 wherein the enzyme catalyses the reduction of $O_2$ to $H_2O$ or $H_2O_2$.

16. A method according to claim 15 wherein the enzyme is $NADH:H_2O$ oxidase including the enzyme having the sequence SEQ ID NO:2.

17. A method according to claim 14 wherein the helper organism is an Ldh⁻ strain.

18. The method of claim 1 in which the helper organism is a Lactococcus.

19. The method of claim 18 in which the helper organism is a *Lactococcus lactis*.

* * * * *

SEQUENCE LISTING

<160> NUMBER OF SEQ ID NOS: 2

<210> SEQ ID NO 1
<211> LENGTH: 1638

<212> TYPE: DNA
<213> ORGANISM: Lactococcus lactis
<220> FEATURE:
<221> NAME/KEY: CDS
<222> LOCATION: (255)..(1580)
<223> OTHER INFORMATION:

<400> SEQUENCE: 1

```
cccgatgctc ccgatgttcg tggaatcatt gaactttcat cagctttggc tgcgggtaca      60
gcttttgatt cagaaactat gtggcaagct taataataaa tctgtcaaaa taatttattt     120
tgacagattt ttttatctaa taattaaaat aattatttca caatgttcac aagcgcttac     180
aaaagaaaat agattgactt atgctaaact gaataatgta aaagaattt tacatttaaa      240 ggagacctat tagt atg aaa atc gta gtt atc ggt aca aac cac gca ggc       290
              Met Lys Ile Val Val Ile Gly Thr Asn His Ala Gly
               1               5                  10 att gct aca gcg aat aca tta ctt gaa caa tat ccc ggg cat gaa att       338
Ile Ala Thr Ala Asn Thr Leu Leu Glu Gln Tyr Pro Gly His Glu Ile
        15                  20                  25 gtc atg att gac cgt aat agc aac atg agt tat cta ggt tgt ggc aca       386
Val Met Ile Asp Arg Asn Ser Asn Met Ser Tyr Leu Gly Cys Gly Thr
    30                  35                  40 gca att tgg gtt gga aga caa att gaa aaa cca gat gaa tta ttt tat       434
Ala Ile Trp Val Gly Arg Gln Ile Glu Lys Pro Asp Glu Leu Phe Tyr
45                  50                  55                  60 gcc aaa gca gag gat ttt gag gca aaa ggg gta aaa att ttg act gaa       482
Ala Lys Ala Glu Asp Phe Glu Ala Lys Gly Val Lys Ile Leu Thr Glu
                65                  70                  75 aca gaa gtt tca gaa att gat ttt gct aat aag aaa gtt tat gca aaa       530
Thr Glu Val Ser Glu Ile Asp Phe Ala Asn Lys Lys Val Tyr Ala Lys
            80                  85                  90 act aaa tct gat gat gaa ata att gaa gct tac gac aag ctt gtt tta       578
Thr Lys Ser Asp Asp Glu Ile Ile Glu Ala Tyr Asp Lys Leu Val Leu
        95                 100                 105 gca aca ggt tca cgt cca att att cct aat cta cca ggc aaa gac ctt       626
Ala Thr Gly Ser Arg Pro Ile Ile Pro Asn Leu Pro Gly Lys Asp Leu
    110                 115                 120 aag gga att cat ttt ctg aaa ctt ttt caa gaa ggt caa gca att gac       674
Lys Gly Ile His Phe Leu Lys Leu Phe Gln Glu Gly Gln Ala Ile Asp
125                 130                 135                 140 gca gaa ttt gcc aaa gaa aaa gtc aag cgt atc gca gtc att ggt gca       722
Ala Glu Phe Ala Lys Glu Lys Val Lys Arg Ile Ala Val Ile Gly Ala
                145                 150                 155 gga tat atc ggt aca gag att gcg gaa gca gct aaa cgt cgg ggt aaa       770
Gly Tyr Ile Gly Thr Glu Ile Ala Glu Ala Ala Lys Arg Arg Gly Lys
            160                 165                 170 gaa gtt ctt ctc ttt gac gct gaa aat act tca ctt gca tca tat tat       818
Glu Val Leu Leu Phe Asp Ala Glu Asn Thr Ser Leu Ala Ser Tyr Tyr
        175                 180                 185 gat gaa gaa ttt gcc aaa gga atg gat gaa aac ctt gct caa cat gga       866
Asp Glu Glu Phe Ala Lys Gly Met Asp Glu Asn Leu Ala Gln His Gly
    190                 195                 200 att gaa ctt cat ttt gga caa ctg gcc aaa gaa ttt aaa gcg aat gag       914
Ile Glu Leu His Phe Gly Gln Leu Ala Lys Glu Phe Lys Ala Asn Glu
205                 210                 215                 220 gaa ggt tat gta tca caa atc gta acc aac aag gcg act tat gat gtt       962
Glu Gly Tyr Val Ser Gln Ile Val Thr Asn Lys Ala Thr Tyr Asp Val
                225                 230                 235 gat ctt gtc atc aat tgt att ggt ttt act gcc aac agt gcc ttg gca      1010
Asp Leu Val Ile Asn Cys Ile Gly Phe Thr Ala Asn Ser Ala Leu Ala
```

-continued

```
                       240                 245                 250
agt gat aag tta gct acc ttc aaa aat ggc gca atc aag gtg gat aag    1058
Ser Asp Lys Leu Ala Thr Phe Lys Asn Gly Ala Ile Lys Val Asp Lys
        255                 260                 265 cat caa caa agt agt gat cca gat gtt tac gcg gta ggt gat gtt gcg    1106
His Gln Gln Ser Ser Asp Pro Asp Val Tyr Ala Val Gly Asp Val Ala
        270                 275                 280 aca att tat tct aat gcc ttg caa gat ttt act tat atc gct ctt gcc    1154
Thr Ile Tyr Ser Asn Ala Leu Gln Asp Phe Thr Tyr Ile Ala Leu Ala
285                 290                 295                 300 tca aac gct gtt cgg tca gga att gtc gca gga cac aat att ggt gga    1202
Ser Asn Ala Val Arg Ser Gly Ile Val Ala Gly His Asn Ile Gly Gly
                305                 310                 315 aaa gaa tta gaa tct gtt ggt gtt caa ggt tct aat ggt att tcg att    1250
Lys Glu Leu Glu Ser Val Gly Val Gln Gly Ser Asn Gly Ile Ser Ile
                320                 325                 330 ttt ggt tac aat atg act tct aca gga ctt tct gtt aaa gct gct aaa    1298
Phe Gly Tyr Asn Met Thr Ser Thr Gly Leu Ser Val Lys Ala Ala Lys
                335                 340                 345 aaa tta ggt tta gaa gtt tca ttt agt gat ttt gaa gat aaa caa aaa    1346
Lys Leu Gly Leu Glu Val Ser Phe Ser Asp Phe Glu Asp Lys Gln Lys
    350                 355                 360 gct tgg ttt ctt cat gaa aac aac gat agt gtg aaa att cgt atc gta    1394
Ala Trp Phe Leu His Glu Asn Asn Asp Ser Val Lys Ile Arg Ile Val
365                 370                 375                 380 tat gag aca aaa agt cgc aga att att gga gca caa ctt gct agt aaa    1442
Tyr Glu Thr Lys Ser Arg Arg Ile Ile Gly Ala Gln Leu Ala Ser Lys
                385                 390                 395 agt gag ata att gca gga aat ata aat atg ttc agt tta gcg att caa    1490
Ser Glu Ile Ile Ala Gly Asn Ile Asn Met Phe Ser Leu Ala Ile Gln
            400                 405                 410 gag aaa aaa aca att gat gaa cta gct ttg ctt gat tta ttc ttt ctc    1538
Glu Lys Lys Thr Ile Asp Glu Leu Ala Leu Leu Asp Leu Phe Phe Leu
            415                 420                 425 ccc cac ttc aac agt cca tat aat tat atg aca gtt gca gct             1580
Pro His Phe Asn Ser Pro Tyr Asn Tyr Met Thr Val Ala Ala
        430                 435                 440 ttgaatgcca aataaacaat agaaatctat ctgcttgata gatttttta ttttttag      1638
```

<210> SEQ ID NO 2
<211> LENGTH: 442
<212> TYPE: PRT
<213> ORGANISM: Lactococcus lactis

<400> SEQUENCE: 2

```
Met Lys Ile Val Val Ile Gly Thr Asn His Ala Gly Ile Ala Thr Ala
1               5                   10                  15

Asn Thr Leu Leu Glu Gln Tyr Pro Gly His Glu Ile Val Met Ile Asp
                20                  25                  30

Arg Asn Ser Asn Met Ser Tyr Leu Gly Cys Gly Thr Ala Ile Trp Val
            35                  40                  45

Gly Arg Gln Ile Glu Lys Pro Asp Glu Leu Phe Tyr Ala Lys Ala Glu
        50                  55                  60

Asp Phe Glu Ala Lys Gly Val Lys Ile Leu Thr Glu Thr Glu Val Ser
65                  70                  75                  80

Glu Ile Asp Phe Ala Asn Lys Val Tyr Ala Lys Thr Lys Ser Asp
                85                  90                  95

Asp Glu Ile Ile Glu Ala Tyr Asp Lys Leu Val Leu Ala Thr Gly Ser
```

-continued

```
                100                 105                 110
Arg Pro Ile Ile Pro Asn Leu Pro Gly Lys Asp Leu Lys Gly Ile His
        115                 120                 125
Phe Leu Lys Leu Phe Gln Glu Gly Gln Ala Ile Asp Ala Glu Phe Ala
        130                 135                 140
Lys Glu Lys Val Lys Arg Ile Ala Val Ile Gly Ala Gly Tyr Ile Gly
145                 150                 155                 160
Thr Glu Ile Ala Glu Ala Ala Lys Arg Arg Gly Lys Glu Val Leu Leu
                165                 170                 175
Phe Asp Ala Glu Asn Thr Ser Leu Ala Ser Tyr Tyr Asp Glu Glu Phe
                180                 185                 190
Ala Lys Gly Met Asp Glu Asn Leu Ala Gln His Gly Ile Glu Leu His
                195                 200                 205
Phe Gly Gln Leu Ala Lys Glu Phe Lys Ala Asn Glu Glu Gly Tyr Val
        210                 215                 220
Ser Gln Ile Val Thr Asn Lys Ala Thr Tyr Asp Val Asp Leu Val Ile
225                 230                 235                 240
Asn Cys Ile Gly Phe Thr Ala Asn Ser Ala Leu Ala Ser Asp Lys Leu
                245                 250                 255
Ala Thr Phe Lys Asn Gly Ala Ile Lys Val Asp Lys His Gln Gln Ser
                260                 265                 270
Ser Asp Pro Asp Val Tyr Ala Val Gly Asp Val Ala Thr Ile Tyr Ser
                275                 280                 285
Asn Ala Leu Gln Asp Phe Thr Tyr Ile Ala Leu Ala Ser Asn Ala Val
        290                 295                 300
Arg Ser Gly Ile Val Ala Gly His Asn Ile Gly Gly Lys Glu Leu Glu
305                 310                 315                 320
Ser Val Gly Val Gln Gly Ser Asn Gly Ile Ser Ile Phe Gly Tyr Asn
                325                 330                 335
Met Thr Ser Thr Gly Leu Ser Val Lys Ala Ala Lys Lys Leu Gly Leu
                340                 345                 350
Glu Val Ser Phe Ser Asp Phe Glu Asp Lys Gln Lys Ala Trp Phe Leu
        355                 360                 365
His Glu Asn Asn Asp Ser Val Lys Ile Arg Ile Val Tyr Glu Thr Lys
        370                 375                 380
Ser Arg Arg Ile Ile Gly Ala Gln Leu Ala Ser Lys Ser Glu Ile Ile
385                 390                 395                 400
Ala Gly Asn Ile Asn Met Phe Ser Leu Ala Ile Gln Glu Lys Lys Thr
                405                 410                 415
Ile Asp Glu Leu Ala Leu Leu Asp Leu Phe Phe Leu Pro His Phe Asn
                420                 425                 430
Ser Pro Tyr Asn Tyr Met Thr Val Ala Ala
        435                 440
```